United States Patent
Hirashita et al.

(10) Patent No.: US 9,722,288 B2
(45) Date of Patent: Aug. 1, 2017

(54) LIQUID ELECTROLYTE FOR BATTERIES, METHOD FOR PRODUCING THE SAME, AND BATTERY COMPRISING THE SAME

(75) Inventors: Tsunehisa Hirashita, Nagoya (JP); Shuki Araki, Nagoya (JP); Katsuyuki Kagami, Nagoya (JP); Hirofumi Nakamoto, Susono (JP); Taishi Shiotsuki, Susono (JP)

(73) Assignees: NAGOYA INSTITUTE OF TECHNOLOGY, Nagoya (JP); TOYOTA JIDOSHA KABUSHIKI KAISHA, Toyota (JP)

( * ) Notice: Subject to any disclaimer, the term of this patent is extended or adjusted under 35 U.S.C. 154(b) by 98 days.

(21) Appl. No.: 14/241,224

(22) PCT Filed: Aug. 28, 2012

(86) PCT No.: PCT/JP2012/071717
§ 371 (c)(1),
(2), (4) Date: Feb. 26, 2014

(87) PCT Pub. No.: WO2013/031776
PCT Pub. Date: Mar. 7, 2013

(65) Prior Publication Data
US 2014/0220476 A1  Aug. 7, 2014

(30) Foreign Application Priority Data

Aug. 30, 2011 (JP) ................... 2011-187937
Mar. 21, 2012 (JP) ................... 2012-063468

(51) Int. Cl.
*H01M 12/08* (2006.01)
*C07D 257/04* (2006.01)
(Continued)

(52) U.S. Cl.
CPC .......... *H01M 12/08* (2013.01); *C07D 257/04* (2013.01); *H01M 10/052* (2013.01);
(Continued)

(58) Field of Classification Search
CPC .......... H01M 10/052; H01M 10/0567; H01M 12/08; H01M 12/06; H01M 2300/0025; C07D 257/04; Y02E 60/122
See application file for complete search history.

(56) References Cited

U.S. PATENT DOCUMENTS

2004/0002002 A1* 1/2004 Mizuta .................. H01G 9/035
429/188
2007/0026318 A1 2/2007 Kishi et al.
(Continued)

FOREIGN PATENT DOCUMENTS

JP  H04-296471 A  10/1992
JP  2003-123838 A   4/2003
(Continued)

OTHER PUBLICATIONS

Machine Translation of WO2008-056776.*
(Continued)

*Primary Examiner* — Stephen Yanchuk
(74) *Attorney, Agent, or Firm* — Oliff PLC

(57) ABSTRACT

An object of the present invention is to provide a liquid electrolyte for batteries, which has excellent ion conductivity, a method for producing the liquid electrolyte and a battery including the liquid electrolyte. Disclosed is a liquid electrolyte for batteries, comprising a mesoionic compound represented by the following general formula (1):

(Continued)

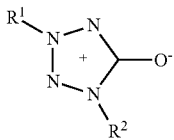

General Formula (1)

wherein R1 and R2 are each independently an alkyl group having 1 to 3 carbon atoms.

7 Claims, 10 Drawing Sheets

(51) Int. Cl.
 *H01M 10/052* (2010.01)
 *H01M 10/0567* (2010.01)
 *H01M 12/06* (2006.01)
(52) U.S. Cl.
 CPC ........ *H01M 10/0567* (2013.01); *H01M 12/06* (2013.01); *H01M 2300/0025* (2013.01); *Y02E 60/128* (2013.01)

(56) References Cited

U.S. PATENT DOCUMENTS

| 2012/0171577 A1 | 7/2012 | Ryu et al. |
| 2012/0219867 A1 | 8/2012 | Nuli et al. |
| 2013/0209915 A1 | 8/2013 | Hirashita et al. |
| 2014/0242473 A1 | 8/2014 | Hirashita et al. |

FOREIGN PATENT DOCUMENTS

| JP | A-2007-35413 | 2/2007 |
| JP | 2007-280627 A | 10/2007 |
| JP | 2012-048874 A | 3/2012 |
| JP | A-2012-94278 | 5/2012 |
| JP | 2012-142196 A | 7/2012 |
| JP | 2012-150924 A | 8/2012 |
| JP | 2012-182124 A | 9/2012 |
| WO | WO 2008/056776 A1 | 5/2008 |
| WO | WO 2012/056292 A1 | 5/2012 |
| WO | 2013/031776 A1 | 3/2013 |

OTHER PUBLICATIONS

STN Search.*
Partial translation of Mar. 17, 2015 Office Action issued in Japanese Application No. 2013-531331.
May 12, 2015 Office Action issued in U.S. Appl. No. 14/192,156.
D. Aurbach et al., "A Short Review on the Comparison Between Li Battery Systems and Rechargeable Magnesium Battery Technology," Journal of Power Sources, 97-98 (2001), pp. 28-32.
O. Tutusaus et al., "An Efficient Halogen-Free Electrolyte for Use in Rechargeable Magnesium Batteries," Angew, Chemistry International Education., 54 (2015), pp. 1-5.
Sep. 2, 2015 Notice of Allowance issued in U.S. Appl. No. 14/192,156.
Dec. 9, 2015 Corrected Notice of Allowability issued in U.S. Appl. No. 14/192,156.

* cited by examiner

LIQUID ELECTROLYTE FOR BATTERIES, METHOD FOR PRODUCING THE SAME, AND BATTERY COMPRISING THE SAME

TECHNICAL FIELD

The present invention relates to a liquid electrolyte for batteries, which has excellent ion conductivity, a method for producing the liquid electrolyte and a battery comprising the liquid electrolyte.

BACKGROUND ART

A secondary battery is a battery that is able to convert chemical energy into electrical energy and discharge the energy. Moreover, it is also a battery that is able to convert electrical energy into chemical energy and store (charge) the chemical energy, by passing electrical current in a direction that is opposite to the direction of current at the time of discharge. Of secondary batteries, a lithium secondary battery has high energy density, so that it is widely used as a power source for portable devices such as a laptop personal computer, a cellular phones etc.

In a lithium secondary battery, when graphite (C) is used as an anode active material, a reaction described by the following formula (I) proceeds at the anode, upon discharge:

$$Li_xC \rightarrow C + xLi^+ + xe^- \qquad (I)$$

wherein $0 < x < 1$.

Electrons generated by the reaction of the formula (I) pass through an external circuit, work by an external load, and then reach the cathode. Lithium ions ($Li^+$) generated by the reaction of the formula (I) are transferred by electro-osmosis from the anode side to the cathode side through an electrolyte sandwiched between the anode and the cathode.

When lithium cobaltate ($Li_{1-x}CoO_2$) is used as a cathode active material, a reaction described by the following formula (II) proceeds at the cathode, upon discharge:

$$Li_{1-x}CoO_2 + xLi^+ + xe^- \rightarrow LiCoO_2 \qquad (II)$$

wherein $0 < x < 1$.

Upon charging the battery, reactions which are reverse to the reactions described by the above formulae (I) and (II) proceed at the anode and the cathode. At the anode, graphite in which lithium has been intercalated by graphite intercalation ($Li_xC$) becomes reusable, while lithium cobaltate ($Li_{1-x}CoO_2$) is regenerated at the cathode. Because of this, discharge becomes possible again.

Conventional lithium secondary batteries are limited in the improvement of reliability, since they use volatile organic solvents.

Meanwhile, a lithium secondary battery that uses an ionic liquid (room-temperature molten-salt) as liquid electrolyte has been known as an effort to improve reliability. "Ionic liquid" as used herein is a salt which is liquid at 100° C. or less, and it is generally non-volatile. Such a liquid electrolyte is advantageous in that it can not only improve reliability but also shows a relatively wide potential window (potential range) and provides a relatively high ion conductivity.

As a lithium secondary battery technique comprising an ionic liquid, a non-aqueous electrolyte secondary battery technique is disclosed in Patent Literature 1, which comprises a cathode, an anode and a non-aqueous electrolyte containing an ionic liquid and allyl phosphate.

In recent years, tetrazolium mesoionic compounds have received attention, due to their wide potential window and low melting point. A tetrazolium mesoionic compound-related technique is disclosed in Patent Literature 2, which has an alkyl or aryl group at the 1-position and an alkyl group at the 3-position.

CITATION LIST

Patent Literature 1: Japanese Patent Application Laid-Open No. 2007-035413
Patent Literature 2: International Publication No. WO2008/056776

SUMMARY OF INVENTION

Technical Problem

An electrolyte is disclosed in paragraph [0090] of the Description of Patent Literature 1, which is obtained by dissolving lithium bis(trifluoromethanesulfonyl)amide, which is a kind of lithium salt, in N-methyl-N-propylpiperidinium bis(trifluoromethanesulfonyl)amide, which is a kind of ionic liquid. However, the inventors of the present invention have studied and found that the electrolyte comprising such a conventional ionic liquid has low ion conductivity.

In Paragraph [0092] of the Description of Patent Literature 2, it is disclosed to apply the tetrazolium mesoionic compound disclosed in this literature to lithium secondary batteries. However, this literature only discloses the melting point, boiling point and cyclic-voltammogram data of the tetrazolium mesoionic compound, and experimental results of the Knoevenagel condensation reaction in the case of using the tetrazolium mesoionic compound as a solvent. Therefore, in this literature, there is no description about the concrete embodiments and effects of the use of the tetrazolium mesoionic compound in a lithium secondary battery.

The present invention was achieved in light of the above circumstances. An object of the present invention is to provide a liquid electrolyte for batteries, which has excellent ion conductivity, a method for producing the liquid electrolyte and a battery comprising the liquid electrolyte.

Solution to Problem

The liquid electrolyte for batteries according to the present invention, comprises a mesoionic compound represented by the following general formula (1):

General Formula (1)

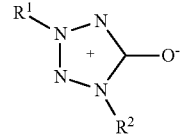

wherein $R^1$ and $R^2$ are each independently an alkyl group having 1 to 3 carbon atoms.

In the present invention, it is preferable that the liquid electrolyte further comprises a lithium salt at a concentration of 0.32 to 1.4 mol/kg.

In the present invention, it is more preferable that the liquid electrolyte further comprises a lithium salt at a concentration of 0.5 to 1.4 mol/kg.

The liquid electrolyte of the present invention can be a liquid electrolyte for lithium-air batteries.

The battery of the present invention comprises at least a cathode, an anode and an electrolyte, the electrolyte being present between the cathode and anode, wherein at least one of the cathode, the anode and the electrolyte comprises the liquid electrolyte.

The method for producing a liquid electrolyte for batteries according to the present invention, comprises the steps of: preparing a lithium salt and a mesoionic compound represented by the general formula (1) and preparing a liquid electrolyte having a water concentration of 200 ppm or less, by mixing at least the lithium salt and the mesoionic compound.

The method of the present invention is preferably such that in the preparation step, the lithium salt is adjusted to have a lithium salt concentration of 0.32 to 1.4 mol/kg in the liquid electrolyte.

The method of the present invention is more preferably such that in the preparation step, the lithium salt is adjusted to have a lithium salt concentration of 0.5 to 1.4 mol/kg in the liquid electrolyte.

The method of the present invention can be a method for producing a liquid electrolyte for lithium-air batteries.

In the method of the present invention, the mesoionic compound can be synthesized under a basic condition, Advantageous Effects of Invention According to the present invention, by containing a mesoionic compound with relatively small molecular size, the viscosity of a liquid electrolyte can be lowered than conventional liquid electrolytes; therefore, the lithium ion conductivity can be increased than conventional liquid electrolytes.

DESCRIPTION OF EMBODIMENTS

1. Liquid Electrolyte for Batteries

The liquid electrolyte for batteries according to the present invention, comprises a mesoionic compound represented by the following general formula (1):

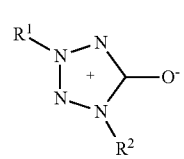

General Formula (1)

wherein $R^1$ and $R^2$ are each independently an alkyl group having 1 to 3 carbon atoms.

A mesoionic compound is a five-membered (or six-membered) heterocyclic compound which is not fully represented by a single covalent bond structure or an ionic structure, and which has a 6π electron in the ring thereof. The mesoionic compound used in the present invention, which has a tetrazolium mesoionic structure, has a five-membered ring composed of four nitrogen atoms and one carbon atom, and is considered to obtain aromaticity and be stabilized by pushing out negative charge into an exocyclic oxygen. The tetrazolium mesoionic compound used in the present invention is turned into an intramolecular salt (that is, an ionic substance) by polarization and is turned into a liquid by selection of alkyl groups. Also, when it is an intramolecular salt, it has a lower boiling point than intermolecular salts and is easy to distill.

As described above, electrolytes comprising conventional ionic liquids have low ion conductivity. The inventors of the present invention have studied and found that the low ion conductivity of conventional electrolytes is due to the high viscosity of conventional ionic liquids.

As a result of diligent researches, the inventors of the present invention have found that a liquid electrolyte comprising the mesoionic compound represented by the above general formula (1) has low volatility, has lower viscosity than conventional liquid electrolytes comprising ionic liquids, and shows outstanding lithium ion conductivity due to, especially in the case of having a high lithium salt concentration, rapid lithium ion transport. Based on these findings, the inventors finally completed the present invention.

Figure 9A:
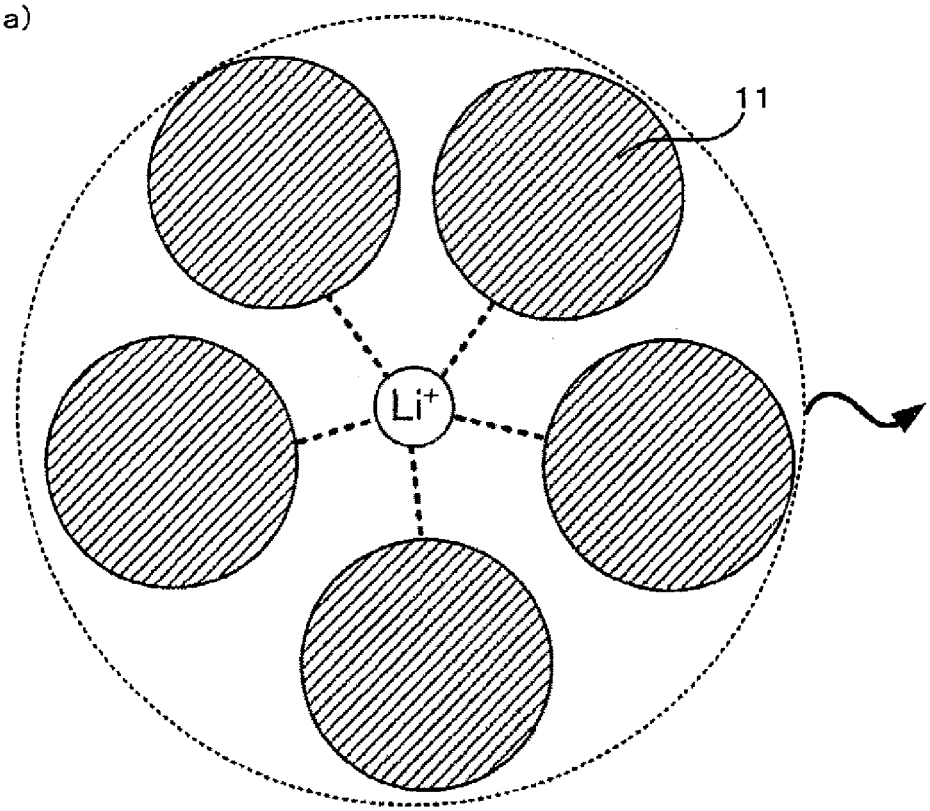
FIG. 9(a) is a schematic view of diffusion in a liquid electrolyte, the liquid electrolyte comprising a lithium salt and an organic solvent and having a relatively low lithium salt concentration.
Figure 9B:
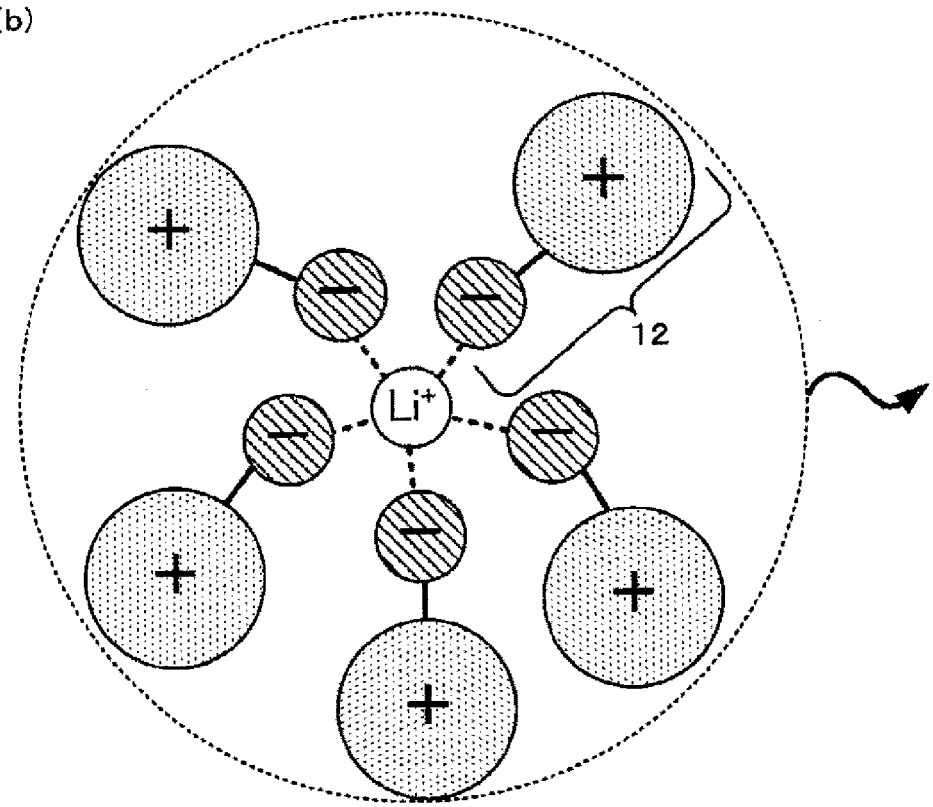
FIG. 9(b) is a schematic view of diffusion in a liquid electrolyte, the liquid electrolyte comprising a lithium salt and a mesoionic compound and having a relatively low lithium salt concentration, and the mesoionic compound having bulky cationic sites.

FIG. 9(a) is a schematic view of diffusion in a liquid electrolyte, the liquid electrolyte comprising a lithium salt and an organic solvent and having a relatively low lithium salt concentration. FIG. 9(b) is a schematic view of diffusion in a liquid electrolyte, the liquid electrolyte comprising a lithium salt and a mesoionic compound and having a relatively low lithium salt concentration, and the mesoionic compound having bulky cationic sites. In FIG. 9(a), each straight dashed line represents a coordinate bond between an organic solvent molecule 11 and a lithium ion. In FIG. 9(b), for the sake of convenience, each mesoionic compound molecule 12 is represented by an anionic site (circle with a minus sign) and a cationic site (circle with a plus sign), the sites being connected to each other by a solid line; moreover, each straight dashed line represents a coordinate bond between the anionic site and a lithium ion. Also in FIGS. 9(a) and 9(b), an aggregate of the lithium ion and the multiple organic solvent molecules or mesoionic compound molecules coordinated with the lithium ion, is represented by a dashed circle.

As shown in FIG. 9(a), in the liquid electrolyte with a relatively low lithium salt concentration, the lithium ion is almost completely coordinated with the multiple organic solvent molecules 11, so that the lithium ion is diffused in an aggregate state in which the multiple organic solvent molecules 11 are solvated. Accordingly, conventional liquid electrolytes comprising bulky organic solvent molecules have a large volume per the aggregate, and this is considered to be a reason for the high viscosity of such conventional liquid electrolytes.

As shown in FIG. 9(b), in the liquid electrolyte with a relatively low lithium salt concentration, the lithium ion is almost completely coordinated with the mesoionic compound molecules 12, so that the lithium ion is diffused in an aggregate state in which the mesoionic compound molecules 12 are solvated. The viscosity of the mesoionic compound having the bulky cationic sites is lower than that of conventional ionic liquids but is higher than that of organic solvents. Therefore, in the liquid electrolyte comprising such a mesoionic compound, it is thought that lithium ions are unlikely to be transported. To realize a further reduction in the low viscosity with no deterioration in the low volatility, which is specific to mesoionic compounds, there is a method for controlling the molecular size of the mesoionic compound and thus decreasing the volume per solvated aggregate.

Figure 1:
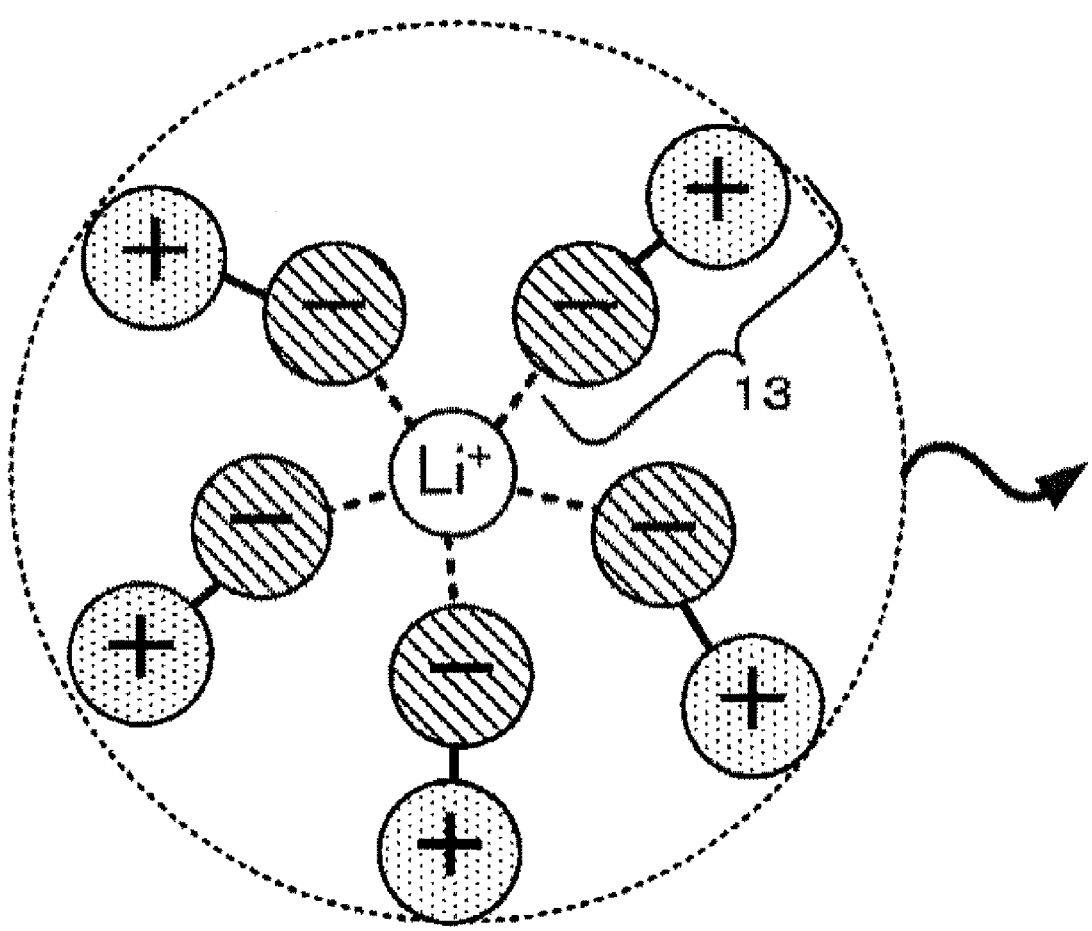
FIG. 1 is a schematic view of diffusion in a liquid electrolyte, the liquid electrolyte comprising a lithium salt and a mesoionic compound and having a relatively low lithium salt concentration, and the mesoionic compound having relatively small cationic sites.

FIG. 1 is a schematic view of diffusion in a liquid electrolyte, the liquid electrolyte comprising a lithium salt and a mesoionic compound and having a relatively low lithium salt concentration, and the mesoionic compound having relatively small cationic sites. Also in FIG. 1, as with FIG. 9(b), for the sake of convenience, each mesoionic compound molecule 13 is represented by an anionic site and a cationic site, the sites being connected to each other by a solid line; moreover, each straight dashed line represents a coordinate bond between the anionic site and a lithium ion. Also in FIG. 1, an aggregate of the lithium ion and the multiple mesoionic compound molecules coordinated with the lithium ion, is represented by a dashed circle.

As shown in FIG. 1, even in the case of using the mesoionic compound having relatively small cationic sites, in the liquid electrolyte with a relatively low lithium salt concentration, the lithium ion is diffused in an aggregate state in which the multiple mesoionic compound molecules 13 are solvated. However, since the cationic sites are relatively small in size, the aggregate itself is also small in volume. As just described, the liquid electrolyte comprising such a mesoionic compound with relatively small cationic site size, has lower viscosity than conventional liquid electrolytes and the lithium ions are likely to disperse; therefore, the liquid electrolyte has higher lithium ion conductivity than conventional liquid electrolytes.

To control the size of the cationic sites, for example, there may be mentioned a method for controlling the alkyl chain length, alkyl group bonding state, etc., of at least one of the following alkyl groups: the alkyl group $R^2$ at the 1-position of the tetrazolium ring shown in the above general formula (1) and the alkyl group $R^1$ at the 3-position of the same.

The alkyl chain length is preferably as short as possible, from the point of view that the size of the aggregate of the lithium ion and the mesoionic compound is further reduced and there is a decrease in the viscosity of the liquid electrolyte. As described above, in the present invention, $R^1$ and $R^2$ are each independently an alkyl group having 1 to 3 carbon atoms. However, it is preferable that the alkyl groups as $R^1$ and $R^2$ have 1 or 2 carbon atoms each, and it is more preferable that one of the alkyl groups as $R^1$ and $R^2$ has 1 carbon atom and the other has 2 carbon atoms.

From the point of view that the size of the aggregate of the lithium ion and the mesoionic compound is further reduced, the alkyl chain is preferably a straight chain, rather than a branched chain. In the present invention, when at least one of the alkyl groups as $R^1$ and $R^2$ has 3 carbon atoms, the group having 3 carbon atoms is preferably n-propyl, rather than i-propyl.

By using a sodium salt, the liquid electrolyte of the present invention can be used for sodium batteries. By using a potassium salt, the liquid electrolyte of the present invention can be used for potassium batteries. Similarly, the liquid electrolyte of the present invention can be used for magnesium batteries, calcium batteries, etc. Also, the liquid electrolyte of the present invention can be used as a liquid electrolyte for primary batteries and that for secondary batteries.

Preferably, the liquid electrolyte of the present invention further comprises a lithium salt, as a supporting salt, in addition to the mesoionic compound. Examples of lithium salts include inorganic lithium salts such as LiOH, $LiPF_6$, $LiBF_4$, $LiClO_4$ and $LiAsF_6$, and organic lithium salts such as $LiCF_3SO_3$, $LiN(SO_2CF_3)_2$(Li-TFSA), $LiN(SO_2C_2F_5)_2$ and $LiC(SO_2CF_3)_3$. Such lithium salts can be used alone or in combination of two or more kinds.

By using a lithium salt, the liquid electrolyte of the present invention can be used for lithium batteries, for example.

The concentration of the lithium salt in the liquid electrolyte of the present invention is preferably 0.10 to 2.4 mol/kg. When the lithium salt concentration is less than 0.10 mol/kg, the lithium salt concentration is too low and the lithium ion amount is too small; therefore, there may be poor lithium ion transport. On the other hand, when the lithium salt concentration is more than 2.4 mol/kg, the lithium salt concentration is too high and thus the viscosity of the liquid electrolyte is too high; therefore, there may be poor lithium ion transport.

The concentration of the lithium salt in the liquid electrolyte of the present invention is more preferably 0.32 mol/kg or more, still more preferably 0.5 mol/kg or more. Also, the lithium salt concentration is more preferably 1.4 mol/kg or less.

As shown under "Examples," especially, a liquid electrolyte for lithium batteries which has a lithium salt concentration of 0.35 mol/kg (Example 3), shows a lithium ion conductivity of 0.66 mS/cm and this is higher than conventional liquid electrolytes. Also, a liquid electrolyte for lithium batteries which has a lithium salt concentration of 0.5 mol/kg (Example 4), shows a lithium ion conductivity of 0.81 mS/cm and this is higher than Example 3.

From the viewpoint of the below-described rapid lithium ion transport, it is particularly preferable that the concentration of the lithium salt in the liquid electrolyte of the present invention is 0.5 to 1.4 mol/kg.

Figure 10A:
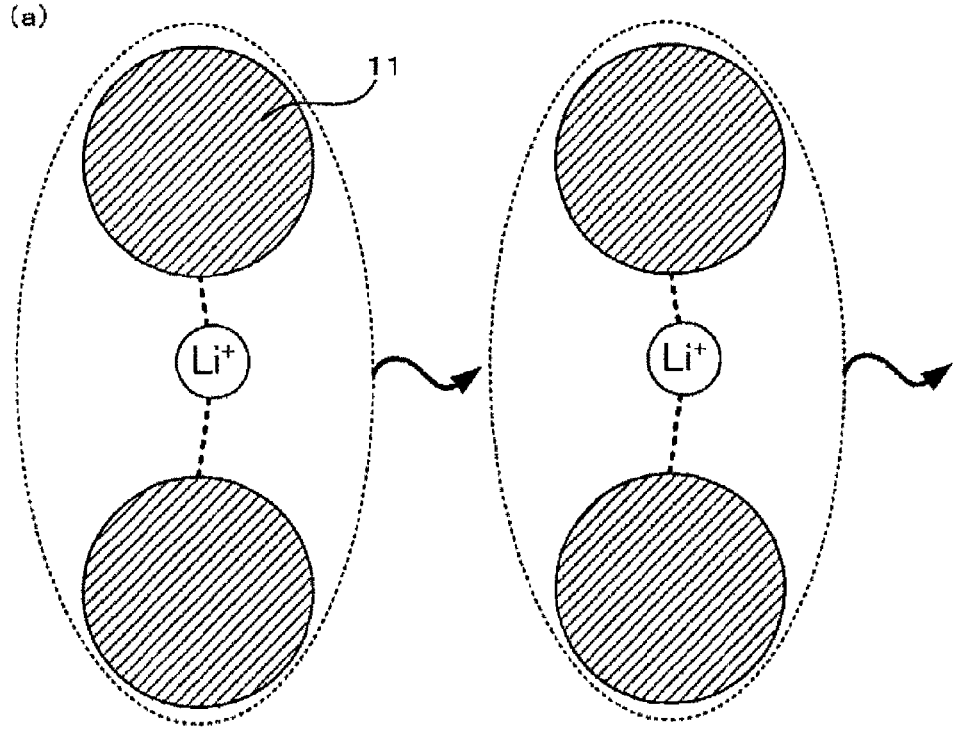
FIG. 10(a) is a schematic view of diffusion in a liquid electrolyte, the liquid electrolyte comprising a lithium salt and an organic solvent and having a relatively high lithium salt concentration.
Figure 10B:
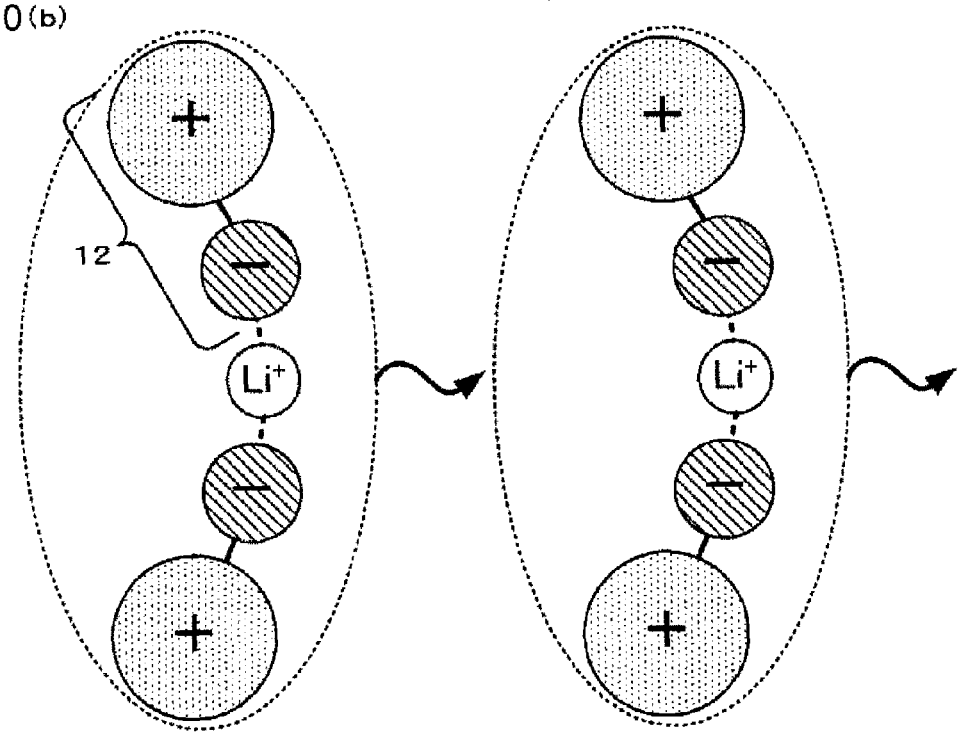
FIG. 10(b) is a schematic view of diffusion in a liquid electrolyte, the liquid electrolyte comprising a lithium salt and a mesoionic compound and having a relatively high lithium. salt concentration, and the mesoionic compound. having bulky cationic sites.

FIG. 10(a) is a schematic view of diffusion in a liquid electrolyte, the liquid electrolyte comprising a lithium salt and an organic solvent and having a relatively high lithium salt concentration. FIG. 10(b) is a schematic view of diffusion in a liquid electrolyte, the liquid electrolyte comprising a lithium salt and a mesoionic compound and having a relatively high lithium salt concentration, and the mesoionic compound having bulky cationic sites. FIGS. 10(a) and 10(b) are similar to FIGS. 9(a) and 9(b) in the following: each dashed line represents a coordinate bond, the anionic and cationic sites of each mesoionic composition molecule are connected by a solid line; and the aggregate including the lithium ion is surrounded by a dashed line.

As shown in FIGS. 10(a) and 10(b), in the liquid electrolyte with a relatively high lithium salt concentration, the solvent coordinated with the lithium ion is smaller than the liquid electrolyte as shown in FIGS. 9(a) and 9(b), which has a relatively low lithium salt concentration.

In general, the organic solvent molecules 11 (a typical example thereof is polycarbonate (PC)) shown in FIG. 10(a) have no partial charge and thus have small interaction with the lithium ion. Therefore, once the coordinate bonds between the lithium ion and the organic solvent molecules 11 are cut, the lithium ion is unlikely to coordinate with the organic solvent molecules and it is thus thought that the lithium ion is dispersed only in an aggregate state in which the organic solvent molecules 11 are solvated.

Each mesoionic compound molecule 12 shown in FIG. 10(b) has a bulky cationic site, so that lithium ion exchange is unlikely to occur between the mesoionic compound molecules 12. Therefore, it is thought that the lithium ion is diffused only in an aggregate state in which the bulky mesoionic compound 12 is solvated.

Figure 2:
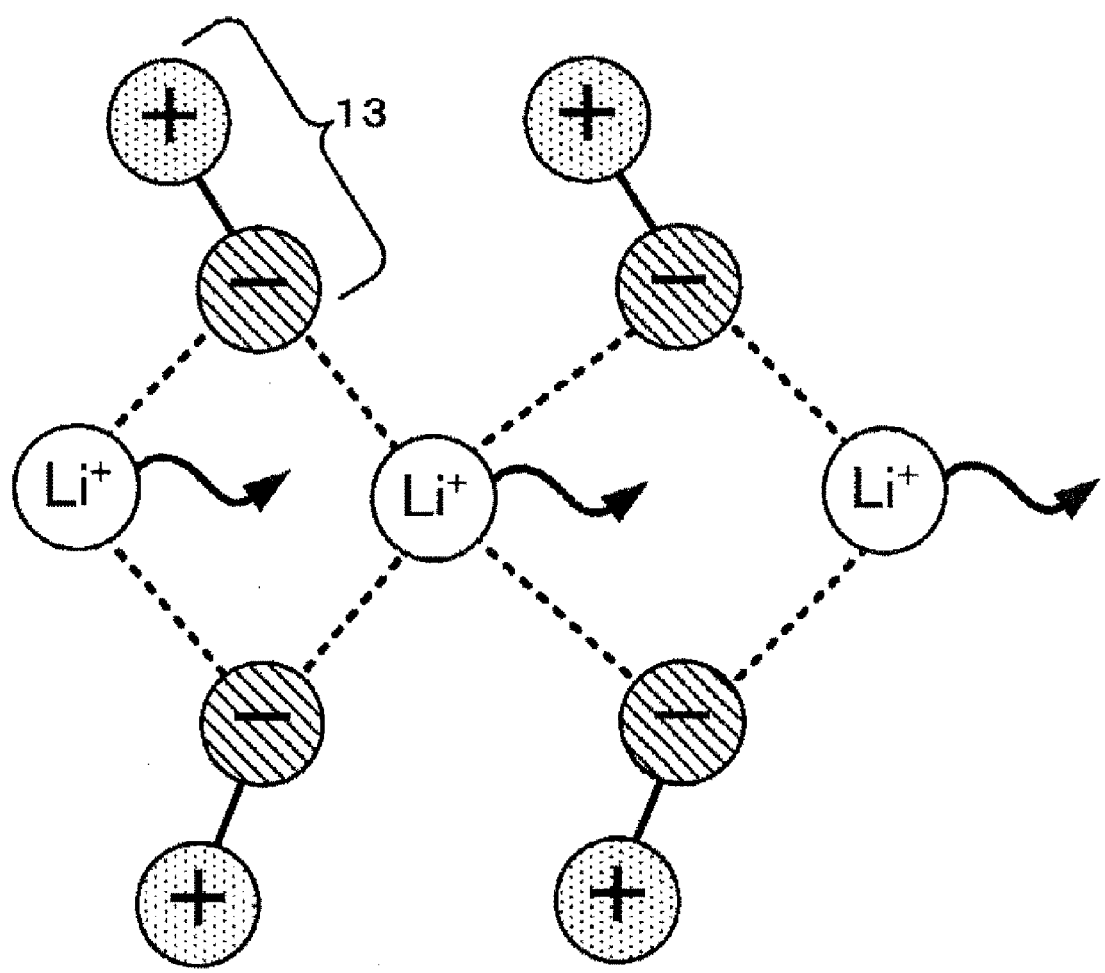
FIG. 2 is a schematic view of diffusion in a liquid electrolyte, the liquid electrolyte comprising a lithium salt and a mesoionic compound and having a relatively high lithium salt concentration, and the mesoionic compound having relatively small cationic sites.

FIG. 2 is a schematic view of diffusion in a liquid electrolyte, the liquid electrolyte comprising a lithium salt and a mesoionic compound and having a relatively high lithium salt concentration, the mesoionic compound having relatively small cationic sites. Also in FIG. 2, as with FIG. 10(b), for the sake of convenience, each mesoionic compound molecule 13 is represented by the anionic and cationic sites connected to each other by a solid line, and each dashed line represents a coordinate bond between each anionic site and the lithium ion.

As shown in FIG. 2, in the case of using the mesoionic compound having relatively small cationic sites, the distance between the mesoionic compound molecules 13 is relatively small. The number of the mesoionic compound molecules 13 is small, relative to the number of the lithium ions; therefore, the interaction between each lithium ion and each mesoionic compound molecule 13 is weakened and thus each lithium ion can coordinate with more of the mesoionic compound molecules 13. As a result, it is though that lithium ion exchange is actively carried out between the mesoionic compound molecules 13 and allows the lithium ions to diffuse alone.

Due to such a large contribution of the so-called rapid lithium ion transport, the suitable liquid electrolyte of the present invention having a relatively high lithium salt concentration of 0.5 to 1.4 mol/kg, has a higher lithium ion conductivity than conventional liquid electrolytes comprising organic solvents or ionic liquids.

In the present invention, the molar ratio between the lithium ion and the mesoionic compound molecules is preferably as follows: lithium ion:mesoionic compound molecules=1:20 to 1:2. When the molar ratio of the mesoionic compound molecules to the lithium ion is too small, the lithium ions are unlikely to dissociate from the anion sites of the mesoionic compound, and rapid lithium ion transport may be inhibited. On the other hand, when the molar ratio of the mesoionic compound molecules to the lithium ion is too large, the lithium ion is completely coordinated with the mesoionic compound molecules to form an aggregate. Therefore, the above-described rapid lithium ion transport effect may not be fully enjoyed.

The molar ratio between the lithium ion and the mesoionic compound molecules (lithium ion:mesoionic compound molecules) is more preferably 1:15 to 1:2.2, still more preferably 1:13 to 1:2.5.

The molar ratio can be calculated from the above-described concentration of the lithium salt in the liquid electrolyte.

The liquid electrolyte of the present invention can further comprise a non-aqueous electrolyte, in addition to the mesoionic compound and the lithium salt.

As the non-aqueous electrolyte, a non-aqueous liquid electrolyte or non-aqueous gel electrolyte can be used.

A non-aqueous liquid electrolyte generally comprises the above-described lithium salt and a non-aqueous solvent. Examples of the non-aqueous solvent include ethylene carbonate (EC), propylene carbonate (PC), dimethyl carbonate (DMC), diethyl carbonate (DEC), ethyl methyl carbonate (EMC), ethyl carbonate, butylene carbonate, γ-butyrolactone, sulfolane, acetonitrile, 1,2-dimethoxyethane, 1,3-dimethoxypropane, diethyl ether, tetrahydrofuran, 2-methyltetrahydrofuran and mixtures thereof. From the point of view that dissolved oxygen can be efficiently used for reaction, the non-aqueous solvent is preferably a solvent with high oxygen solubility. In the non-aqueous liquid electrolyte, the lithium salt concentration is in the range of 0.5 to 3 mol/L, for example.

The non-aqueous gel electrolyte used in the present invention is generally a non-aqueous liquid electrolyte gelled by addition of a polymer. For example, it can be obtained by adding a polymer such as polyethylene oxide (PEO), polyacrylonitrile (PAN) or polymethyl methacrylate (PMMA) to the above-described non-aqueous liquid electrolyte for gelation. In the present invention, for example, there may be used LiTFSA (LiN (CF$_3$SO$_2$)$_2$)-PEO-based non-aqueous gel electrolytes.

The applications of the liquid electrolyte of the present invention are not particularly limited, as long as they are applications as materials for batteries. For example, the liquid electrolyte of the present invention can be used as an electrolyte which functions to exchange ions between electrodes and as an electrolyte for electrodes which can increase ion conductivity of electrodes.

The type of battery in which the liquid electrolyte of the present invention is used, is not particularly limited.

For example, the liquid electrolyte of the present invention can be used in a lithium-air battery, as a liquid electrolyte for lithium-air batteries, and in an air or secondary battery that uses the above-described other metal ions.

2. Battery

The battery of the present invention comprises at least a cathode, an anode and an electrolyte, the electrolyte being present between the cathode and anode, wherein at least one of the cathode, the anode and the electrolyte comprises the liquid electrolyte.

Figure 3:
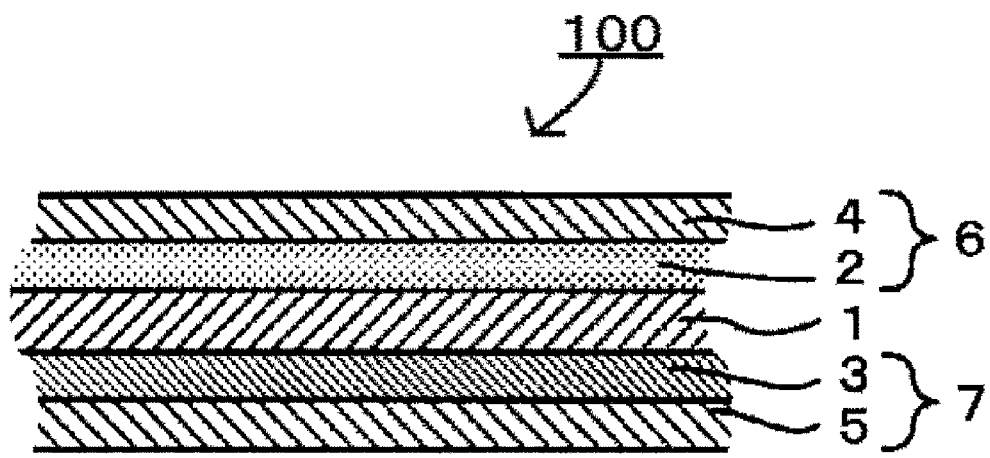
FIG. 3 is a view showing an example of the layer structure of the battery according to the present invention, and it is also a view schematically showing a cross section of the battery cut along the laminating direction.

FIG. 3 is a view showing an example of the layer structure of the battery according to the present invention, and it is also a view schematically showing a cross section of the battery cut along the laminating direction. However, the battery of the present invention is not limited to this example.

A battery 100 comprises a cathode 6, an anode 7 and an electrolyte 1, the cathode 6 comprising a cathode active material layer 2 and a cathode current collector 4, the anode 7 comprising an anode active material layer 3 and an anode current collector 5, and the electrolyte 1 being sandwiched between the cathode 6 and the anode V.

In the present invention, at least one of the cathode, the anode and the electrolyte comprises the liquid electrolyte of the present invention. Hereinafter, the cathode, anode and electrolyte, which constitute the battery of the present invention, and a separator and a battery case, which are suitably used in the battery of the present invention, will be described in detail.

The cathode used in the present invention preferably comprises a cathode active material layer which comprises a cathode active material. In addition, the cathode generally comprises a cathode current collector and a cathode lead that is connected to the cathode current collector. When the battery of the present invention is an air battery, the battery comprises an air electrode, in place of the cathode, which comprises an air electrode layer.

Hereinafter, a case where a cathode comprising a cathode active material layer is used as the cathode, will be explained.

Concrete examples of cathode active materials that can be used in the present invention, include $LiCoO_2$, $LiNi_{1/3}Mn_{1/3}Co_{1/3}O_2$, $LiNiPO_4$, $LiMnPO_4$, $LiNiO_2$, $LiMn_2O_4$, $LiCoMnO_4$, $Li_2NiMn_3O_8$, $Li_3Fe_2(PO_4)_3$ and $Li_3V_2(PO_4)_3$. Among them, in the present invention, it is preferable to use $LiCoO_2$ as the cathode active material.

The thickness of the cathode active material layer used in the present invention varies depending on the intended use of the battery, etc. However, the thickness is preferably 10 to 250 µm, more preferably 20 to 200 µm, still more preferably 30 to 150 µm.

The cathode active material preferably has an average particle diameter of 1 to 50 µm, more preferably 1 to 20 µm, still more preferably 3 to 5 µm. When the average particle diameter of the cathode active material is too small, there is a possibility of poor handling properties. When the average particle diameter of the cathode active material is too large, there may be a difficulty in obtaining a flat cathode active material layer. The average particle diameter of the cathode active material can be obtained by, for example, measuring the particle diameters of active material carrier particles observed with a scanning electron microscope (SEM) and averaging the particle diameters.

As needed, the cathode active material layer can contain an electroconductive material, a binder, etc.

The electroconductive material used in the present invention is not particularly limited, as long as it can increase the electrical conductivity of the cathode active material layer. The examples include carbon blacks such as acetylene black and Ketjen Black. The content of the electroconductive material in the cathode active material layer varies depending on the type of the electroconductive material; however, it is generally 1 to 10% by mass.

As the binder used in the present invention, for example, there may be mentioned polyvinylidene fluoride (PVDF) and polytetrafluoroethylene (PTFE). The content of the binder in the cathode active material layer is required to be a content which allows the cathode active material and so on to be fixed, and is preferably as small as possible. The content of the binder is generally 1 to 10% by mass.

The cathode current collector used in the present invention functions to collect current from the cathode active material layer. Examples of materials for the cathode current collector include aluminum, stainless-steel (SUS), nickel, iron and titanium, and preferred are aluminum and stainless-steel (SUS). Examples of the form of the cathode current collector include a foil form, a plate form and a mesh form. Preferred is a foil form.

The cathode active material layer can further contain an electrolyte for the cathode. In this case, as the electrolyte for the cathode, there may be used not only the liquid electrolyte of the present invention but also the below-described liquid electrolyte, gel electrolyte, solid electrolyte, etc.

The method for producing the cathode used in the present invention is not particularly limited, as long as it is a method that can provide the above-described cathode. After forming the cathode active material layer, the cathode active material layer can be pressed to increase electrode density.

Hereinafter, a case where an air electrode comprising an air electrode layer is used as the cathode, will be explained. The air electrode layer used in the present invention comprises at least an electroconductive material. As needed, the air electrode layer can further contain at least one of a catalyst and a binder.

The electroconductive material used in the present invention is not particularly limited, as long as it is electrically conductive. As the material, for example, there may be mentioned a carbonaceous material, etc. The carbonaceous material can be porous or non-porous. It is preferably porous in the present invention, so that it has a large specific surface area and offers many reaction sites. As the porous carbonaceous material, in particular, there may be mentioned mesoporous carbon, etc. As the non-porous carbonaceous material, in particular, there may be mentioned graphite, acetylene black, carbon nanotubes, carbon fibers, etc. The content of the electroconductive material in the air electrode layer is preferably 65 to 99% by mass, more preferably 75 to 95% by mass. This is because when the content of the electroconductive material is too small, the area of reaction sites is decreased, resulting in a possible decrease in battery capacity. On the contrary, when the content of the electroconductive material is too large, the content of the catalyst becomes relatively small, resulting in a possibility of poor catalyst performance.

As the catalyst for the air electrode used in the present invention, for example, there may be mentioned cobalt phthalocyanine, manganese dioxide, etc. The content of the catalyst in the air electrode layer is preferably 1 to 30% by mass, more preferably 5 to 20% by mass. This is because when the content of the catalyst is too small, there is a possibility of poor catalyst performance; moreover, when the content of the catalyst is too large, the content of the electroconductive material becomes relatively small, so that the area of reaction sites is decreased and results in a possible decrease in battery capacity.

From the viewpoint of smooth electrode reaction, the above-described electroconductive material preferably supports the catalyst.

The air electrode layer is needed to contain at least the electroconductive material. However, it is more preferable that the air electrode layer further contains a binder for fixing the electroconductive material. As the binder, for example, there may be mentioned polyvinylidene fluoride (PVDF), polytetrafluoroethylene (PTFE), etc. The content of the binder in the air electrode layer is not particularly limited. However, it is preferably 30% by mass or less, more preferably 1 to 10% by mass.

The thickness of the air electrode layer varies depending on the application of the air battery, etc. However, it is preferably 2 to 500 μm, more preferably 5 to 300 μm.

The air electrode layer can further contain an electrolyte for the air electrode. In this case, as the electrolyte for the air electrode, there may be used the liquid electrolyte of the present invention: moreover, there may be used the below-described liquid electrolyte, gel electrolyte and solid electrolyte, etc.

In addition to the air electrode layer, the air electrode used in the present invention can comprise an air electrode current collector and an air electrode lead that is connected to the air electrode current collector.

The air electrode current collector used in the present invention functions to collect current from the air electrode layer. The material for the air electrode current collector is not particularly limited, as long as it is electrically conductive. For example, there may be mentioned stainless-steel, nickel, aluminum, iron, titanium and carbon. As the form of the air electrode current collector, there may be mentioned a foil form, a plate form and a mesh (grid) form, for example. Of these, in the present invention, the air electrode current collector is preferably in a mesh form. This is because the air electrode current collector in such a form has excellent current collection efficiency. In this case, normally, the air electrode current collector in a mesh form is provided inside the air electrode layer. In addition, the battery of the present invention can comprise a different air electrode current collector (such as a current collector in a foil form) that collects current collected by the air electrode current collector in a mesh form. Also in the present invention, the below-mentioned battery case can also function as the air electrode current collector.

The thickness of the air electrode current collector is preferably 10 to 1,000 μm, more preferably 20 to 400 μm.

The anode used in the present invention preferably comprises an anode active material layer comprising an anode active material. In general, it further comprises an anode current collector and an anode lead that is connected to the anode current collector.

The anode active material layer used in the present invention comprises an anode active material comprising at least one selected from the group consisting of a metal material, an alloy material and a carbonaceous material. The anode active material used for the anode active material layer is not particularly limited, as long as it can at least store or release metal ions. When the battery of the present invention is a lithium battery, lithium metal, lithium alloys, lithium-containing metal oxides, lithium-containing metal sulfides, lithium-containing metal nitrides, carbonaceous materials such as graphite, etc., can be used for the anode active material. The anode active material can be in a powder form or a thin film form.

Examples of lithium alloys include a lithium-aluminum alloy, a lithium-tin alloy, a lithium-lead alloy and a lithium-silicon alloy. Examples of lithium-containing metal oxides include a lithium-titanium oxide. Examples of lithium-containing metal nitrides include a lithium-cobalt nitride, a lithium-iron nitride and a lithium-manganese nitride. Also, a solid electrolyte-coated lithium can be used for the anode active material layer.

The anode active material layer can comprise only the anode active material, or it can comprise at least one of the electroconductive material and the binder, in addition to the anode active material. For example, when the anode active material is in the form of a foil, the anode active material layer can be an anode active material layer comprising only the anode active material. When the anode active material is in the form of powder, the anode active material layer can be an anode active material layer comprising the anode active material and the binder. The electroconductive material and the binder are the same as those that can be used for the cathode active material layer or the air electrode layer.

The thickness of the anode active material layer is not particularly limited; however, it is preferably 10 to 100 μm, more preferably 10 to 50 μm.

The anode active material layer can further contain an electrolyte for the anode. In this case, as the electrolyte for the anode, there may be used not only the liquid electrolyte of the present invention but also the below-described liquid electrolyte, gel electrolyte, solid electrolyte, etc.

As the material for and the form of the anode current collector, there may be used those mentioned above as the material for and the form of the cathode current collector.

The electrolyte used in the present invention is sandwiched between the cathode and the anode and functions to exchange metal ions therebetween.

As the electrolyte, there may be used a liquid electrolyte, a gel electrolyte, a solid electrolyte, etc. They may be used alone or in combination of two or more kinds.

As the liquid electrolyte, there may be used a non-aqueous liquid electrolyte or an aqueous liquid electrolyte.

As the aqueous liquid electrolyte used in the present invention, one containing water and a metal salt is generally used. When the metal battery according to the present invention is a lithium battery, a lithium salt can be used as the metal salt. Examples of the lithium salt include LiOH, LiCl, $LiNO_3$ and $CH_3CO_2Li$.

The non-aqueous liquid electrolyte used in the present invention is the same as the non-aqueous liquid electrolyte that can be used in the above-described liquid electrolyte for batteries. However, depending on the type of battery used, there may be used other metal salt such as a potassium salt or sodium salt, in place of the lithium salt.

The liquid electrolyte used in the present invention can contain the liquid electrolyte of the present invention. The liquid electrolyte used in the present invention can be the liquid electrolyte itself of the present invention.

The gel electrolyte used in the present invention is the same as the non-aqueous gel electrolyte that can be used for the above-described liquid electrolyte for batteries. However, depending on the type of battery used, there may be used other metal salt such as a potassium salt or sodium salt, in place of the lithium salt.

As the solid electrolyte, there may be used a sulfide solid electrolyte, an oxide solid electrolyte, a polymer electrolyte, etc.

Concrete examples of sulfide solid electrolytes include $Li_2S$—$P_2S_5$, $Li_2S$—$P_2S_3$, $Li_2S$—$P_2S_3$—$P_2S_5$, $Li_2S$—$SiS_2$, $Li_2S$—$Si_2S$, $Li_2S$—$B_2S_3$, $Li_2S$—$GeS_2$, $LiI$—$Li_2S$—$P_2S_5$, $LiI$—$Li_2S$—$SiS_2$—$P_2S_5$, $Li_2S$—$SiS_2$—$Li_4SiO_4$, $Li_2S$—$SiS_2$—$Li_3PO_4$, $Li_3PS_4$—$Li_4GeS_4$, $Li_{3.4}P_{0.6}Si_{0.4}S_4$, $Li_{3.25}P_{0.25}Ge_{0.76}S_4$ and $Li_{4-x}Ge_{1-x}P_xS_4$.

Concrete examples of oxide solid electrolytes include LiPON (lithium phosphorus oxynitride), $Li_{1.3}Al_{0.3}Ti_{0.7}(PO_4)_3$, $La_{0.51}Li_{0.34}TiO_{0.74}$, $Li_3PO_4$, $Li_2SiO_2$ and $Li_2SiO_4$.

The polymer electrolyte used in the present invention generally contains a metal salt and a polymer. When the metal battery according to the present invention is a lithium battery, a lithium salt can be used as the metal salt. As the lithium salt, there may be used at least one of the above-mentioned inorganic and organic lithium salts. The polymer is not particularly limited as long as it can form a complex with a lithium salt. As the polymer, for example, there may be mentioned polyethylene oxide.

As the solid electrolyte used in the present invention, in addition to the above, there may be mentioned $Li_2Ti(PO_4)_3$—$AlPO_4$ (Ohara glass), for example.

In the battery of the present invention, a separator infiltrated with the above-described liquid electrolyte can be present between the cathode and anode. As the separator, for example, there may be mentioned polyolefin-based porous films such as those made of polyethylene and polypropylene, and non-woven fabrics such as a resin non-woven fabric and a glass fiber non-woven fabric.

The battery of the present invention generally comprises a battery case for housing the cathode, the liquid electrolyte, the anode and so on. As the form of the battery case, in particular, there may be mentioned a coin form, a flat plate form, a cylinder form and a laminate form, for example.

When the battery of the present invention is an air battery, the battery case can be an open-to-the-atmosphere battery case or closed battery case. The open battery case is one that has a structure in which at least the air electrode layer can be sufficiently exposed to the air. On the other hand, when the battery case is a closed battery case, it is preferable that the closed battery case is equipped with gas (air) inlet and outlet tubes. In this case, it is preferable that the introduced/emitted gas has a high oxygen concentration, and it is more preferable that the introduced/emitted gas is pure oxygen. It is also preferable that the oxygen concentration is high at the time of discharge and low at the time of charge.

3. Method for Producing a Liquid Electrolyte for Batteries

The method for producing a liquid electrolyte for batteries, comprising the steps of: preparing a lithium salt and a mesoionic compound represented by the general formula (1) and preparing a liquid electrolyte having a water concentration of 200 ppm or less, by mixing at least the lithium salt and the mesoionic compound.

Hereinafter, an example of the method for producing the mesoionic compound used in the present invention, will be explained. However, the method for producing the mesoionic compound used in the present invention is not limited to this example.

The production example comprises the following steps (1) and (2):

(1) the step of producing a tetrazole-5-thione derivative which has an alkyl group having 1 to 3 carbon atoms at the 1-position; and (2) the step of producing a tetrazolium-5-olate derivative which has alkyl groups at the 1- and 3-positions, the alkyl groups having 1 to 3 carbon atoms each and being independent from each other.

Hereinafter, the steps (1) and (2) will be explained in detail.

First, in the step (1), as shown by the following reaction formula (a), alkaline azide ($MN_3$; M is an alkali metal) is reacted with alkyl isothiocyanate ($R^2NCS$) to synthesize a tetrazole-5-thione derivative which has an alkyl group, $R^2$, having 1 to 3 carbon atoms at the 1-position.

As the alkyl isothiocyanate, for example, there may be used the following: methyl isothiocyanate ($CH_3NCS$) can be used when the alkyl group $R^2$ has one carbon atom; ethyl isothiocyanate ($C_2H_5NCS$) can be used when the alkyl group $R^2$ has two carbon atoms; and propyl isothiocyanate ($C_3H_7NCS$) can be used when the alkyl group $R^2$ has three carbon atoms.

Formula (a)

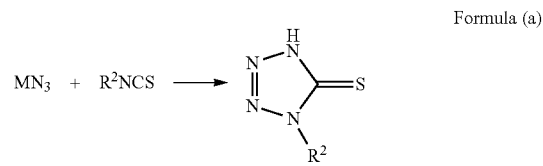

Next, in the step (2), as shown by the following reaction formula (b), the tetrazole-5-thione derivative synthesized in the step (1) is alkylated by an alkylating agent and then hydrolyze by a base to synthesize a tetrazolium-5-olate derivative which has alkyl groups at the 1- and 3-positions, the alkyl groups having 1 to 3 carbon atoms each and being independent from each other.

The alkylating agent is not particularly limited, as long as it can introduce an alkyl group having 1 to 3 carbon atoms into the 3-position of the tetrasol ring. For example, there may be used dialkyl sulfate, alkali metal alkoxide, alkyl triflate, etc. The base is not particularly limited as long as it can inactivate the excess alkylating agent and hydrolyze the thus-obtained alkylated thiotetrazole derivative.

As the alkylating agent, for example, there may be used the following: at least one of sodium methoxide ($NaOCH_3$) and dimethyl sulfate ($(CH_3O)_2SO_2$) can be used when the alkyl group $R^1$ has one carbon atom; at least one of sodium ethoxide ($NaOC_2H_5$) and diethyl sulfate ($(C_2H_5O)_2SO_2$) is used when the alkyl group $R^1$ has two carbon atoms; and at least one of sodium propoxide ($NaOC_3H_7$) and dipropyl sulfate ($(C_3H_7O)_2SO_2$) can be used when the alkyl group $R^1$ has three carbon atoms.

As the base, for example, there may be used inorganic bases such as potassium hydroxide and sodium hydroxide, and aqueous solutions thereof.

Formula (b)

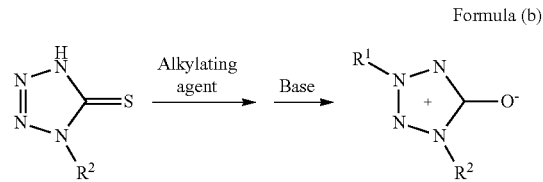

As shown by the above reaction formulae (a) and (b), the mesoionic compound used in the present invention can be one synthesized under a basic condition. Under a neutral or acidic condition, especially the reaction shown by the reaction formula (b) may not proceed. When completing the reaction (quenching), the reaction solution can be made neutral or acidic.

The mesoionic compound represented by the above general formula (1) is preferably used under a neutral or basic condition. For example, when heated under an acidic condition, the mesoionic compound may be broken.

In the step of producing the liquid electrolyte for batteries, at least the mesoionic compound and a lithium salt are mixed to produce a liquid electrolyte for batteries, the liquid electrolyte having a water concentration of 200 ppm or less. The lithium salt used for the liquid electrolyte is as described above.

Especially by setting the water concentration to 100 ppm or less, battery materials which may deteriorate by reaction with water can be used for batteries in combination with the liquid electrolyte for batteries, thus expanding the range of battery material choices. Examples of battery materials which may deteriorate by reaction with water include lithium metals, sulfide solid electrolytes, etc.

To produce the liquid electrolyte for batteries having a water concentration of 100 ppm or less, for example, there may be mentioned a method in which a liquid of the mesoionic compound is distilled to sufficiently remove water and then mixed with a lithium salt in a glove box under an inert atmosphere. As the lithium salt, non-hydrates are more preferred than hydrates. To measure the water concentration, for example, there may be used the distillation method defined in JIS K 2275, the Karl Fischer capacity titration method, the Karl Fischer coulometric titration method, or a hydrate reaction method. In the Karl Fischer capacity titration method and Karl Fischer coulometric titration method, there may be used a commercially-available Karl Fischer water content meter.

The water content in the liquid electrolyte for batteries is preferably as small as possible. For example, the lower limit of the water content in the liquid electrolyte can be 0.1 ppm or 1 ppm.

EXAMPLES

Hereinafter, the present invention further described in detail, by way of examples and comparative examples. However, the present invention is not limited to these examples.

1. 1-Ethyl-3-methyltetrazolium-5-olate

First, as the above-described step (1), the synthesis of 1-ethyl tetrazole-5-thione was carried out, according to the following reaction formula ($a_1$):

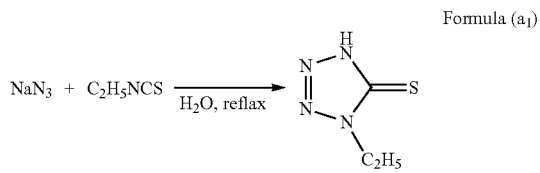

Formula ($a_1$)

In particular, 4 mL of water, 0.2 g of sodium azide (manufactured by Kanto Chemical Co., Inc.) and 0.17 mL of ethyl isothiocyanate (manufactured by Tokyo Chemical Industry Co., Ltd.) were put in a recovery flask and reacted under a reflux condition for 20 hours. After cooling the mixture, 0.43 g of a sodium hydroxide aqueous solution (obtained by dissolving NaOH (manufactured by Nacalai Tesque, Inc.) in 10 mL water) was added thereto to make the mixture a basic mixture (pH>13). Then, the basic mixture was washed with methylene chloride (manufactured by Wako Pure Chemical Industries, Ltd.) Then, 2.0 mL of 35% concentrated hydrochloric acid (manufactured by Sigma-Aldrich Corporation) was added to an aqueous layer thus formed to acidify the mixture (pH<1). Then, ether (manufactured by Yoneyama Yakuhin Kogyo Co., Ltd.) was added thereto to extract the target product from the aqueous layer. An ether layer thus formed was dried with anhydrous sodium sulfate (manufactured by Sigma-Aldrich Corporation) and then the solvent was removed therefrom by distillation, thus obtaining 1-ethyl tetrazole-5-thione (light yellow liquid, 0.20 g, yield 76%).

1-Ethyltetrazole-5-thione $^1$HNMR (200 MHz, CDCl$_3$): δ1.54 (t, J=7.4 Hz, 3H), 4.35 (q, J=7.2 Hz, 2H)

$^1$HNMR (300 MHz, DMSO-d$_6$): δ1.36 (t, J=7.4 Hz, 3H), 4.23 (q, J=7.2 Hz, 2H)

Next, as the above-described step (2), 1-ethyl-3-methyltetrazolium-5-olate was synthesized according to the following reaction formula ($b_1$):

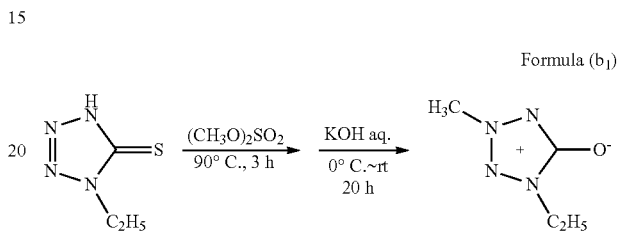

Formula ($b_1$)

In particular, 4.54 g of 1-ethyl tetrazole-5-thione and 13.2 mL of dimethyl sulfate (manufactured by Nacalai Tesque, Inc.) were put in a recovery flask and stirred at 90° C. for 3 hours. After cooling and then icing the reaction mixture, the mixture was gradually added to a potassium hydroxide aqueous solution (obtained by dissolving 9.85 g of KOH (manufactured by Nacalai Tesque, Inc.) in 200 mL water) in an ice bath. After reaching room temperature, the reaction mixture was stirred for 20 hours. To a reaction solution thus obtained, 4.0 mL of 35% concentrated hydrochloric acid (manufactured by Sigma-Aldrich Corporation) was added to acidify the solution (pH<1). Then, the solution was washed with ether (manufactured by Yoneyama Yakuhin Kogyo Co., Ltd.) In addition, 3.2 g of potassium hydroxide (manufactured by Nacalai Tesque, Inc.) was added thereto to make an aqueous layer thus formed a basic layer (pH>13). Methylene chloride (manufactured by Wako Pure Chemical Industries, Ltd.) was added thereto to extract the target product from the aqueous layer. A methylene chloride layer thus obtained and an ether layer thus obtained were dried with anhydrous sodium sulfate (manufactured by Sigma-Aldrich Corporation) and then the solvent was removed from the layers by distillation. Of them, from the methylene chloride layer, 1-ethyl-3-methyltetrazolium-5-olate (yellow solid, 2.3 g, yield 48%) was obtained. This yellow solid could be purified by Kugelrohr distillation (170° C., 3 mmHg) (final yield: 1.1 g, isolated yield 25%).

1-Ethyl-3-methyltetrazolium-5-olate $^1$HNMR (200 MHz, CDCl$_3$): δ1.45 (t, J=7.4 Hz, 3H), 4.06 (q, J=7.4 Hz, 2H), 4.11 (s, 3H)

MS (EI): m/z 128 (100, M$^+$), 57 (14)

2. Synthesis of 1-butyl-3-methyltetrazolium-5-olate

1-Butyl-3-methyltetrazolium-5-olate was obtained in the same manner as the synthesis method of 1-ethyl-3-methyltetrazolium-5-olate, through the two-step reaction process, except that butyl isothiocyanate (manufactured by Tokyo Chemical Industry Co., Ltd.) was used in the above step (1), in place of ethyl isothiocyanate (manufactured by Tokyo Chemical Industry Co., Ltd.)

3. Production of Liquid Electrolytes for Lithium Batteries

Example 1

First, 1-ethyl-3-methyltetrazolium-5-olate (hereinafter may be referred to as EMTO) was synthesized by the above method and mixed with lithium bis(trifluoromethanesulfonyl)amide (hereinafter may be referred to as LiTFSA) (manufactured by Kojundo Chemical Laboratory Co., Ltd.) so as to have a lithium salt concentration of 0.1 mol/kg. After homogenously dissolving the mixture, the mixture was stirred for 3 hours, thus producing the liquid electrolyte for lithium batteries of Example 1.

Example 2

First, EMTO was synthesized by the above method and mixed with LiTFSA so as to have a lithium salt concentration of 0.32 mol/kg. After homogenously dissolving the mixture, the mixture was stirred for 3 hours, thus producing the liquid electrolyte for lithium batteries of Example 2.

Example 3

First, EMTO was synthesized by the above method and mixed with LiTFSA so as to have a lithium salt concentration of 0.35 mol/kg. After homogenously dissolving the mixture, the mixture was stirred for 3 hours, thus producing the liquid electrolyte for lithium batteries of Example 3.

Example 4

First, EMTO was synthesized by the above method and mixed with LiTFSA so as to have a lithium salt concentration of 0.5 mol/kg. After homogenously dissolving the mixture, the mixture was stirred for 3 hours, thus producing the liquid electrolyte for lithium batteries of Example 4.

Example 5

First, EMTO was synthesized by the above method and mixed with LiTFSA so as to have a lithium salt concentration of 1.4 mol/kg. The mixture was homogenously dissolved by heating to 80° C. and then stirred for 3 hours, thus producing the liquid electrolyte for lithium batteries of Example 5.

Example 6

First, EMTO was synthesized by the above method and mixed with LiTFSA so as to have a lithium salt concentration of 2.6 mol/kg. The mixture was homogenously dissolved by heating to 80° C. and then stirred for 3 hours, thus producing the liquid electrolyte for lithium batteries of Example 6.

Comparative Example 1

First, 1-butyl-3-methyltetrazolium-5-olate (hereinafter may be referred to as BMTO) was synthesized by the above method and mixed with LiTFSA so as to have a lithium salt concentration of 0.1 mol/kg. The mixture was homogenously dissolved and then stirred for 3 hours, thus producing the liquid electrolyte for lithium batteries of Comparative Example 1.

Comparative Example 2

First, BMTO was synthesized by the above method and mixed with LiTFSA so as to have a lithium salt concentration of 0.32 mol/kg. The mixture was homogenously dissolved and then stirred for 3 hours, thus producing the liquid electrolyte for lithium batteries of Comparative Example 2.

Comparative Example 3

First, BMTO was synthesized by the above method and mixed with LiTFSA so as to have a lithium salt concentration of 0.35 mol/kg. The mixture was homogenously dissolved and then stirred for 3 hours, thus producing the liquid electrolyte for lithium batteries of Comparative Example 3.

Comparative Example 4

First, BMTO was synthesized by the above method and mixed with LiTFSA so as to have a lithium salt concentration of 0.5 mol/kg. The mixture was homogenously dissolved and then stirred for 3 hours, thus producing the liquid electrolyte for lithium batteries of Comparative Example 4.

Comparative Example 5

First, N-methyl-N-propylpiperidinium bis(trifluoromethanesulfonyl)amide (hereinafter may be referred to as PP13TFSA) (manufactured by Kanto Chemical Co., Inc.) was mixed with LiTFSA so as to have a lithium salt concentration of 0.32 mol/kg. The mixture was homogenously dissolved and then stirred for 3 hours, thus producing the liquid electrolyte for lithium batteries of Comparative Example 5.

Comparative Example 6

First, PP13TFSA (manufactured by Kanto Chemical Co., Inc.) was mixed with LiTFSA so as to have a lithium salt concentration of 0.35 mol/kg. The mixture was homogenously dissolved and then stirred for 3 hours, thus producing the liquid electrolyte for lithium batteries of Comparative Example 6.

Comparative Example 7

First, N,N-diethyl-N-methyl-N-methoxyethyl ammonium bis(trifluoromethanesulfonyl)amide (hereinafter may be referred to as DEMETFSA) (manufactured by Kanto Chemical Co., Inc.) was mixed with LiTFSA so as to have a lithium salt concentration of 0.35 mol/kg. The mixture was homogenously dissolved and then stirred for 3 hours, thus producing the liquid electrolyte for lithium batteries of Comparative Example 7.

4. Viscosity Measurement of Liquid Electrolytes for Lithium Batteries

The viscosities of the liquid electrolytes of Example 2 and Comparative Examples 2 and 5 were measured. Details of the measurement condition are as follows.

Measurement device: viscometer (VM-10A manufactured by CBC Co., Ltd.)

Measurement temperature: 60° C.

Figure 4:
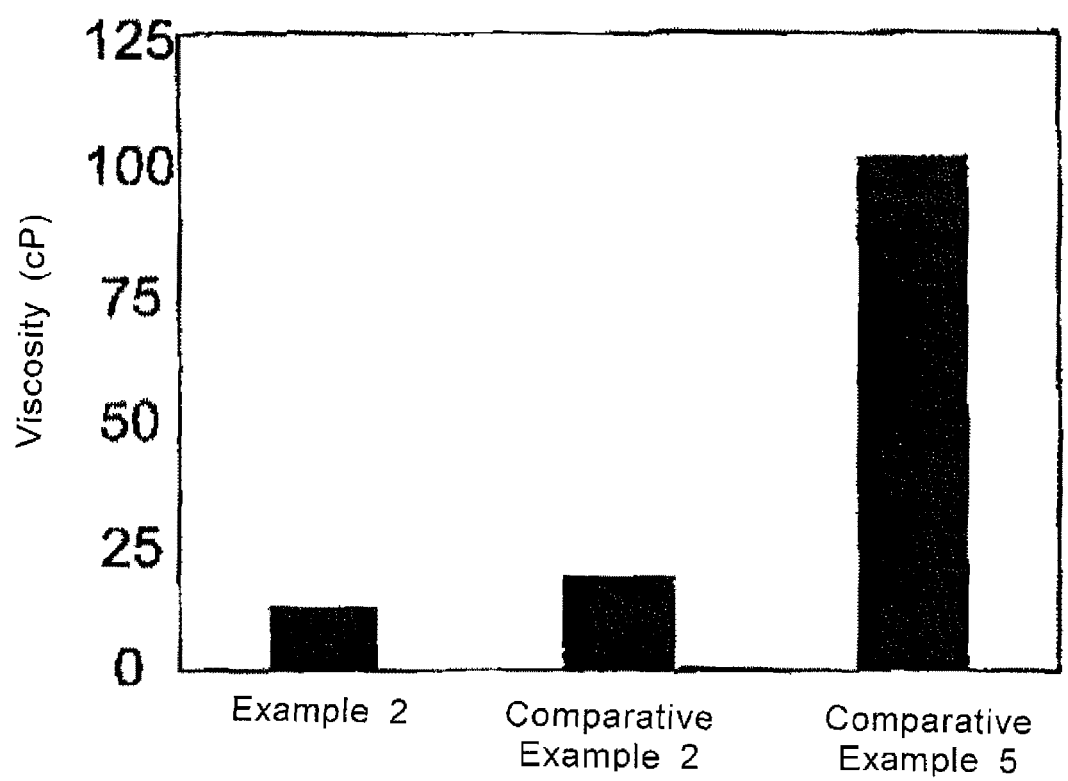
FIG. 4 is a bar graph comparing the viscosities of liquid electrolytes of Example 2 and Comparative Examples 2 and 5.

FIG. 4 is a bar graph comparing the viscosities of the liquid electrolytes of Example 2 and Comparative Examples 2 and 5. The liquid electrolyte of Comparative Example 5, which comprises PP13TFSA, has a viscosity of 102 cP. The liquid electrolyte of Comparative Example 2, which comprises BMTO, has a viscosity of 18.5 cP. The liquid electrolyte of Example 2, which comprises EMTO, has a viscosity of 11.5 cP and this is the lowest viscosity among the liquid electrolytes of Example 2 and Comparative Examples 2 and 5.

From the viscosity comparison results shown in FIG. 4, it is clear that although the liquid electrolytes of Example 2 and Comparative Examples 2 and 5 have the same lithium salt concentration, the liquid electrolyte of Example 2 has a lower viscosity than those of Comparative Examples 2 and 5, along with maintaining low volatility.

5. Lithium Ion Conductivity Measurement of Liquid Electrolytes for Lithium Batteries First, the ion conductivities of the liquid electrolytes of Examples 1 to 6 and Comparative Examples 1 to 5 were measured. Details of the measurement condition are as follows.
Measurement device: Conductivity meter (SevenMulti-A manufactured by Mettler-Toledo International Inc.)
Measurement temperature: 60° C.

Next, magnetic field gradient NMR measurement was performed on the liquid electrolytes of Examples 1 to 6 and Comparative Examples 1 to 4. From the measurement results, the diffusion coefficient $D_{Li}$ of $^7$Li (lithium cation) and the diffusion coefficient $D_F$ of $^{19}$F (fluorine anion) were calculated. Details of the magnetic field gradient NMR measurement condition are as follows.
NMR: Manufactured by JEOL Ltd.
Measurement temperature: 60° C.
g: 300 to 1,100 (G/cm) (Li), 150 to 700 (G/cm) (F)
δ: 4 (ms) (Li), 2 (ms) (F)
Δ: 50 (ms)

The diffusion coefficients $D_{Li}$ and $D_F$ were each calculated by the following Stejskal-Tanner equation (c):

$$E = \frac{S}{S_0} = \exp\left(-\gamma^2 g^2 \delta^2 D\left(\Delta - \frac{\delta}{3}\right)\right) \quad \text{Equation (c)}$$

wherein E is the peak intensity ratio; S is the peak intensity; $S_0$ is the peak intensity measured when there is no magnetic field gradient; γ is the gyromagnetic ratio of nuclear spin; g is the magnetic field gradient intensity; δ is the magnetic field gradient irradiation time; D is the diffusion coefficient $D_{Li}$ or $D_F$; and Δ is the time interval between magnetic field irradiations.

The lithium ion transport numbers ($t_{Li}$) of the liquid electrolytes of Examples 1 to 6 and Comparative Examples 1 to were determined by the following equation (d), using the values of $D_{Li}$ and $D_F$:

$$t_{Li} = D_{Li}/(D_{Li} + D_F) \quad \text{Equation (d)}$$

Magnetic field gradient NMR measurement was performed on the liquid electrolytes of Comparative Examples 5 to 7. From the measurement results, the diffusion coefficient $D_H$ of $^1$H (proton) and the diffusion coefficients $D_{Li}$ and $D_F$ were calculated. The condition of the magnetic field gradient NMR measurement is the same as above, except that at the time of measurement of $^1$H (proton), the magnetic field gradient irradiation time δ was set to 4 (ms).

The lithium ion transport numbers ($t_{Li}$) of the liquid electrolyte of Comparative Examples 5 and 6 were determined by the following equation ($e_1$), using the values of $D_{Li}$, $D_F$ and $D_H$, and the values of $C_{LiTFSA}$ (the concentration of LiTFSA), $M_{LiTFSA}$ (the molecular weight of LiTFSA) and $M_{PP13TFSA}$ (the molecular weight of PP13TFSA).

$$t_{Li} = \frac{C_{LiTFSA} \cdot D_{Li}}{C_{LiTFSA} \cdot D_{Li} + \left(C_{LiTFSA} + \frac{1000 - C_{LiTFSA} \cdot M_{LiTFSA}}{M_{PP13TFSA}}\right) \cdot D_F + A} \quad \text{Equation (e}_1\text{)}$$

$$\left(\text{wherein } A = \left(\frac{1000 - C_{LiTFSA} \cdot M_{LiTFSA}}{M_{PP13TFSA}}\right) \cdot D_H\right)$$

The lithium ion transport number ($t_{Li}$) of the liquid electrolyte of Comparative Example 7 was determined by the following equation ($e_2$), using the values of $D_{Li}$, $D_F$ and $D_H$, and the values of $C_{LiTFSA}$, $M_{LiTFSA}$ and $M_{DEMETFSA}$ (the molecular weight of DEMETFSA).

$$t_{Li} = \frac{C_{LiTFSA} \cdot D_{Li}}{C_{LiTFSA} \cdot D_{Li} + \left(C_{LiTFSA} + \frac{1000 - C_{LiTFSA} \cdot M_{LiTFSA}}{M_{DEMETFSA}}\right) \cdot D_F + A} \quad \text{Equation (e}_2\text{)}$$

$$\left(\text{wherein } A = \left(\frac{1000 - C_{LiTFSA} \cdot M_{LiTFSA}}{M_{DEMETFSA}}\right) \cdot D_H\right)$$

The lithium ion conductivities of the liquid electrolytes are measured by the following equation (f):

Lithium ion conductivity = ion conductivity × lithium ion transport number ($t_{Li}$)     Equation (f)

Figure 5:
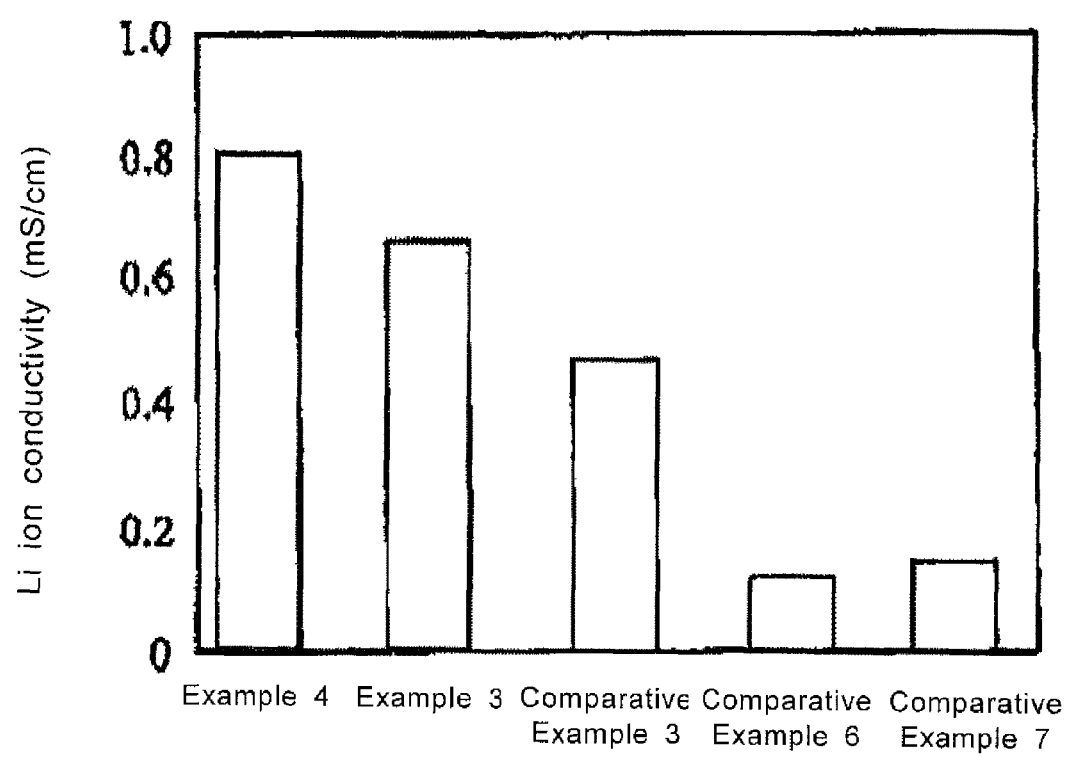
FIG. 5 is a bar graph comparing the lithium ion conductivities of liquid electrolytes for lithium batteries of Examples 3 and 4 and Comparative Examples 3, 6 and 7.

FIG. 5 is a bar graph comparing the lithium ion conductivities of liquid electrolytes for lithium batteries of Examples 3 and 4 and Comparative Examples 3, 6 and 7. The liquid electrolyte of Comparative Example 7, comprising DEMETFSA and having lithium salt concentration of 0.35 mol/kg, has a lithium ion conductivity of 0.17 mS/cm. The liquid electrolyte of Comparative Example 6, comprising PP13TFSA and having a lithium salt concentration of 0.35 mol/kg, has a lithium ion conductivity of 0.13 mS/cm. The liquid electrolyte of Comparative Example 3, comprising BMTO and having a lithium salt concentration of 0.35 mol/kg, has a lithium ion conductivity of 0.44 mS/cm. On the other hand, the liquid electrolyte of Example 3, comprising EMTO and having a lithium salt concentration of 0.35 mol/kg, has a lithium ion conductivity of 0.66 mS/cm. The liquid electrolyte of Example 4, comprising EMTO and having a lithium salt concentration of 0.5 mol/kg, has a lithium ion conductivity of 0.81 mS/cm. The value of Example 4 is the highest among the liquid electrolytes of Examples 3 and 4 and Comparative Examples 3, 6 and 7.

From the lithium ion conductivity comparison results shown in FIG. 5, it is clear that although the liquid electrolytes of Examples 3 and 4 and Comparative Examples 3, 6 and 7 have the same lithium salt concentration, the liquid electrolyte of Example 3 can exhibit better lithium ion conductivity than the liquid electrolytes of Comparative Examples 3, 6 and 7, along with maintaining low volatility. It is also clear that by increasing the lithium salt concentration to 0.5 mol/kg as in Example 4, more excellent lithium ion conductivity can be achieved.

Figure 6:
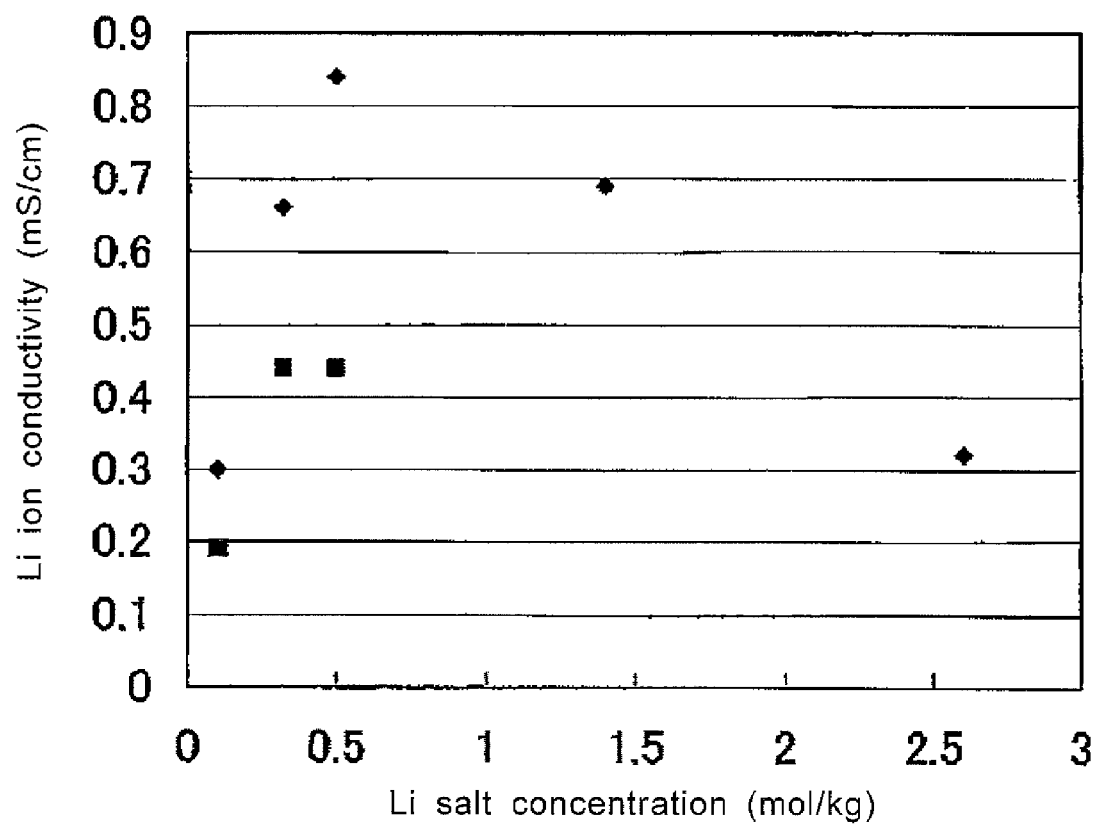
FIG. 6 is a graph comparing the lithium ion conductivities of liquid electrolytes for lithium batteries of Examples 1, 2, 4 to 6 and Comparative Examples 1, 2 and 4.

FIG. 6 is a graph comparing the lithium ion conductivities of liquid electrolytes for lithium batteries of Examples 1, 2, 4 to 6 and Comparative Examples 1, 2 and 4. It is also a graph with lithium ion conductivity (mS/cm) on the vertical axis and lithium salt concentration (mol/kg) on the horizontal axis. In FIG. 6, plotted black rhombuses indicate the data of Examples 1, 2, 4 to 6, each comprising EMTO, and plotted black squares indicates the data of Comparative Examples 1, 2 and 4, each comprising BMTO.

The following is clear from FIG. 6: the lithium ion conductivity of the liquid electrolyte comprising BMTO is 0.19 mS/cm when the lithium salt concentration is 0.1 mol/kg (Comparative Example 1), 0.44 mS/cm when the lithium salt concentration is 0.32 mol/kg (Comparative Example 2) and 0.44 mS/cm when the lithium ion concentration is 0.5 mol/kg (Comparative Example 4).

On the other hand, the lithium ion conductivity of the liquid electrolyte comprising EMTO is 0.30 mS/cm when the lithium salt concentration is 0.1 mol/kg (Example 1), 0.66 mS/cm when the lithium salt concentration is 0.32 mol/kg (Example 2), 0.81 mS/cm when the lithium salt concentration is 0.5 mol/kg (Example 4), 0.69 mS/cm when the lithium salt concentration is 1.4 mol/kg (Example 5) and 0.32 mS/cm when the lithium salt concentration is 2.6 mol/kg (Example 6).

From comparisons between Example 1 and Comparative Example 1 (both having the same lithium salt concentration of 0.1 mol/kg), between Example 2 and Comparative Example 2 (both having the same lithium salt concentration of 0.32 mol/kg) and between Example 4 and Comparative Example 4 (both having the same lithium salt concentration of 0.5 moi/kg), it is clear that the lithium ion conductivities of Examples 1, 2 and 4, all of which comprise EMTO, are 1.5 or more times higher than the lithium ion conductivities of Comparative Examples 1, 2 and 4, all of which comprise BMTO.

6. Calculation of Electrical Conductivity Due to Rapid Lithium Ion Transport First, for the liquid electrolytes of Examples 1, 2, 4 to 6 and Comparative Examples 1, 2 and 4, the lithium ion conductivity due to free diffusion was obtained by the following equation (g). The degrees of lithium salt dissociation of these liquid electrolytes were assumed to be constant, regardless of their lithium salt concentrations.

Lithium ion conductivity due to free diffusion
=(lithium ion valence×lithium salt concentration×lithium salt dissociation degree)/viscosity     Equation (g)

Next, using the thus-obtained value of lithium ion conductivity due to free diffusion, the electrical conductivity due to rapid lithium ion transport by the following equation (h):

Electrical conductivity due to rapid lithium ion transport =lithium ion conductivity−lithium ion conductivity due to free diffusion     Equation (h)

Figure 7:
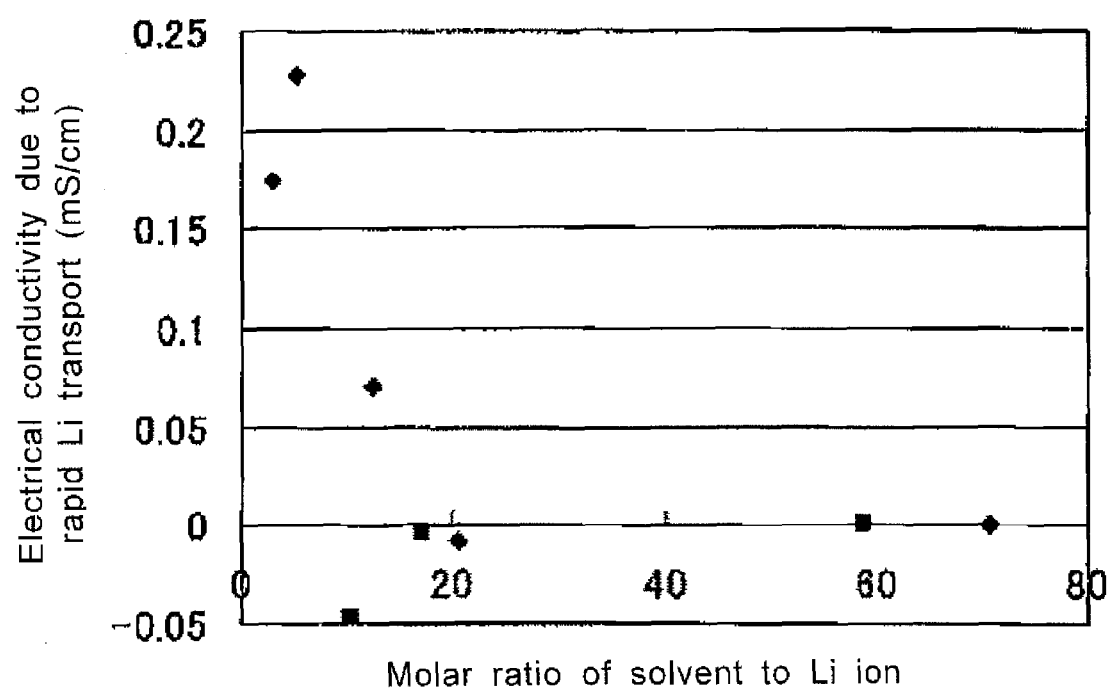
FIG. 7 is a graph comparing the electrical conductivities of liquid electrolytes for lithium batteries of Examples 1, 2, 4 to 6 and Comparative Examples 1, 2 and 4, the electrical conductivities being due to rapid lithium ion transport.

FIG. 7 is a graph comparing the electrical conductivities of the liquid electrolytes for lithium batteries of Examples 1, 2, 4 to 6 and Comparative Examples 1, and 4, the electrical conductivities being due to rapid lithium ion transport. It is also a graph with the electrical conductivity due to rapid lithium ion transport (mS/cm) on the vertical axis and the molar ratio of the solvent (mesoionic compound) to the lithium ions on the horizontal axis. In FIG. 7, plotted black rhombuses indicate the data of Examples 1, 2, 4 to 6, each comprising EMTO, and plotted black squares indicate the data of Comparative Examples 1, 2 and 4, each comprising BMTO. Also in FIG. 7, the molar ratio of the solvent (mesoionic compound) to the lithium ions is a ratio of the amount of substance (molar amount) of the solvent molecules (mesoionic compound molecules) to the lithium ions (1 mol).

The following is clear from FIG. 7: the electrical conductivity due to rapid lithium ion transport of the liquid electrolyte comprising BMTO, is 0 mS/cm when the molar ratio of the solvent to the lithium ions is 58.8 (Comparative Example 1), 0 mS/cm when the molar ratio is 17.2 (Comparative Example 2), and −0.05 mS/cm when the molar ratio is 10.4 (Comparative Example 4).

On the other hand, as is clear from FIG. 7, the electrical conductivity due to rapid lithium ion transport of the liquid electrolyte comprising EMTO, is 0 mS/cm when the molar ratio of the solvent to the lithium ions is 70.8 (Example 1), −0.01 mS/cm when the molar ratio is 20.7 (Example 2), 0.07 mS/cm when the molar ratio is 12.5 (Example 4), 0.23 mS/cm when the molar ratio is 5.2 (Example 5) and 0.17 mS/cm when the molar ratio is 2.8 (Example 6).

From the results shown in FIG. 7, it is clear that among the liquid electrolytes comprising EMTO, the electrical conductivity due to rapid lithium ion transport is extremely higher in the liquid electrolytes of Examples 4 to 6, in each which the molar ratio of the solvent to the lithium ions is 2.8 to 12.5, compared to the remaining liquid electrolytes.

From the above results, the inventors of the present invention have succeeded in improving the electrical conductivity due to rapid lithium ion transport of the liquid electrolytes comprising EMTO, which is almost impossible in conventional liquid electrolytes for lithium batteries, by optimizing the molar ratio of the solvent to the lithium ions.

7. Production of Lithium-Air Battery

Example 7

Ketjen Black (ECP600JD, hereinafter may be referred to as KB) was used as the electroconductive material, and PTFE (F-104 manufactured by Daikin Industries, Ltd.) was used as the binder. The electroconductive material and the binder were mixed at the following ratio: KB:PTFE=90% by mass:10% by mass. The mixture was formed into an air electrode pellet. One obtained by injecting 50 μL of the liquid electrolyte for lithium batteries of Example 4 (EMTO containing LiTFSA at a lithium salt concentration of 0.5 mol/kg) into the air electrode pellet was used as the air electrode.

$Li_2Ti(PO_4)_3$—$AlPO_4$ (OHARA glass, manufactured by Ohara Inc.) was used as an electrolyte. As the separator, one obtained by injecting 50 μL of the liquid electrolyte for lithium batteries of Comparative Example 7 (DEMETFSA containing LiTFSA at a lithium salt concentration of 0.35 mol/kg) into a polyolefin-based separator (manufactured by Nippon Sheet Glass Co., Ltd.), was used. A lithium metal was used as the anode.

The air electrode, electrolyte, separator and anode were stacked in this sequence, thus producing the lithium-air battery of Example 7.

Example 8

The lithium-air battery of Example 8 was produced in the same manner as Example 7, except that 50 μL of the liquid electrolyte for lithium batteries of Example 2 (EMTO containing LiTFSA at a lithium salt concentration of 0.32 mol/kg) was injected in to the air electrode pellet, instead of injecting 50 μL of the liquid electrolyte of Example 4

(EMTO containing LiTFSA at a lithium salt concentration of 0.5 mol/kg) into the air electrode pellet.

Example 9

The lithium-air battery of Example 9 was produced in the same manner as Example 7, except that 50 μL of the liquid electrolyte for lithium batteries of Example 5 (EMTO containing LiTFSA at a lithium salt concentration of 1.4 mol/kg) was injected into the air electrode pellet, instead of injecting 50 μL of the liquid electrolyte of Example 4 (EMTO containing LiTFSA at a lithium salt concentration of 0.5 mol/kg) into the air electrode pellet.

Comparative Example 8

The lithium-air battery of Comparative Example 8 was produced in the same manner as Example 7, except that 50 μL of the liquid electrolyte for lithium batteries of Comparative Example 7 (DEMETFSA containing LiTFSA at a lithium salt concentration of 0.35 mol/kg) was injected into the air electrode pellet, instead of injecting 50 μL of the liquid electrolyte of Example 4 (EMTO containing LiTFSA at a lithium salt concentration of 0.5 mol/kg) into the air electrode pellet.

8. IV Test

Figure 8:
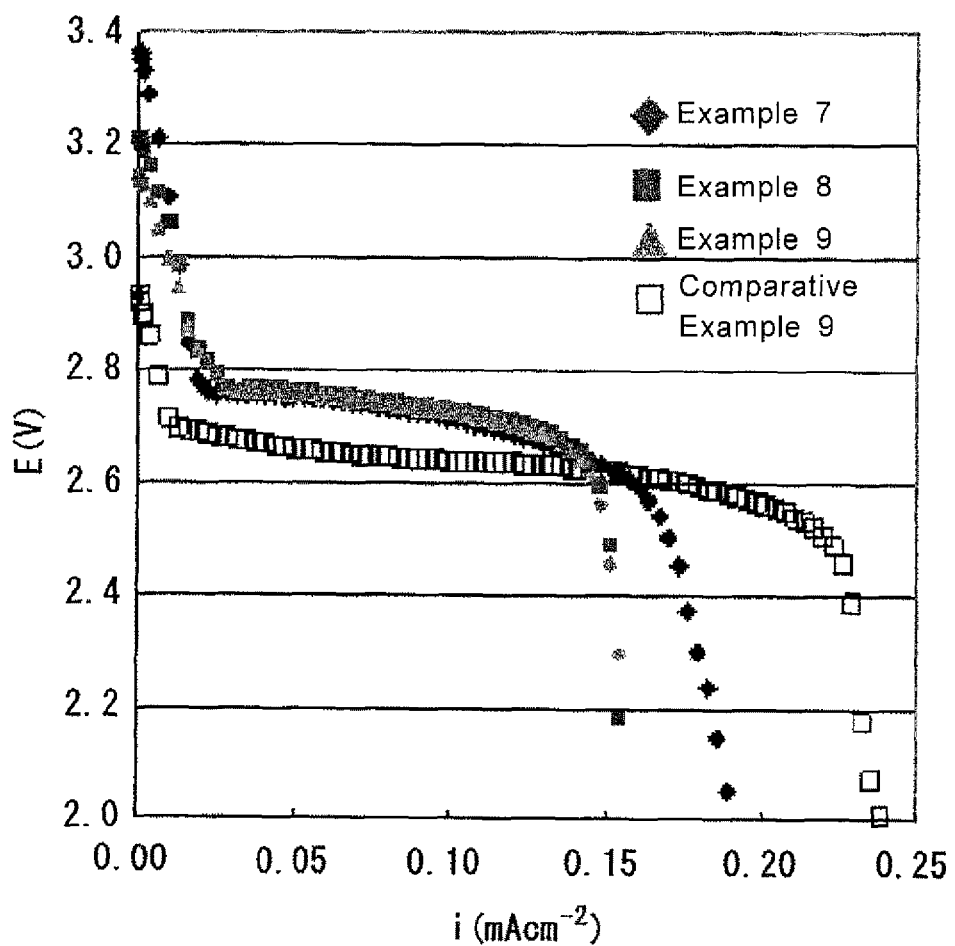
FIG. 8 is a graph showing the discharge IV characteristics of lithium-air batteries of Examples 7 to 9 and Comparative Example 8.

The IV test was performed on the lithium-air batteries of Examples 7 to 9 and Comparative Example 8, with changing the current density to be measured. Details of the test are as follows:
Atmosphere: Pure oxygen
Electrode area: 2.5 cm$^2$
Test temperature: 60° C.
Constant current holding time: 30 Minutes
FIG. 8 is a graph showing the discharge IV characteristics of lithium-air batteries of Examples 7 to 9 and Comparative Example 8. As is clear from FIG. 8, while the lithium-air battery of Comparative Example 8 starts to discharge from 2.7 V, the lithium-air batteries of Examples 7 to 9 start to discharge from 2.8 V.

In practical aspects, the difference of 0.1 V in discharge starting voltage is extremely important. Higher capacity and higher output are required of lithium-air batteries. In lithium-air batteries, an increase in discharge starting voltage contributes to achieving both higher capacity and higher output. Therefore, the battery of the present invention can respond to the need for both higher capacity and higher output.

REFERENCE SIGNS LIST

1. Electrolyte
2. Cathode active material layer
3. Anode active material layer
4. Cathode current collector
5. Anode current collector
6. Cathode
7. Anode
11. Organic solvent molecule
12. Mesoionic compound molecule having a bulky cationic site
13. Mesoionic compound molecule having a relatively small cationic site
100. Battery

The invention claimed is:

1. A liquid electrolyte for batteries, comprising a mesoionic compound represented by the following general formula (1) and a lithium salt at a concentration of 0.5 to 1.4 mol/kg:

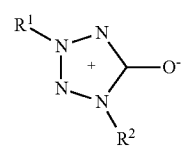

General Formula (1)

wherein $R^1$ and $R^2$ are each independently an alkyl group having 1 to 3 carbon atoms, and
wherein a molar ratio between a lithium ion of the lithium salt and mesoionic compound molecules (lithium ion: mesoionic compound molecules) in the liquid electrolyte is from 1:12.5 to 1:5.2.

2. The liquid electrolyte according to claim 1, being a liquid electrolyte for lithium-air batteries.

3. A battery comprising at least a cathode, an anode and an electrolyte, the electrolyte being present between the cathode and anode,
wherein at least one of the cathode, the anode and the electrolyte comprises the liquid electrolyte defined by claim 1.

4. A method for producing a liquid electrolyte for batteries, comprising the steps of:
preparing a lithium salt and a mesoionic compound represented by the following general formula (1):

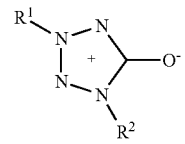

General Formula (1)

wherein $R^1$ and $R^2$ are each independently an alkyl group having 1 to 3 carbon atoms, and
preparing a liquid electrolyte having a water concentration of 200 ppm or less, a lithium salt concentration of 0.5 to 1.4 mol/kg, and a molar ratio between a lithium ion of the lithium salt and mesoionic compound molecules (lithium ion: mesoionic compound molecules) of from 1:12.5 to 1:5.2, by mixing at least the lithium salt and the mesoionic compound.

5. The method according to claim 4, being a method for producing a liquid electrolyte for lithium-air batteries.

6. The method according to claim 4, wherein the mesoionic compound is synthesized under a basic condition.

7. The liquid electrolyte according to claim 1, wherein a lithium ion conductivity at 60° C. obtained by the following Equation (f) is 0.69 to 0.81 mS/cm:

$$\text{lithium ion conductivity} = \text{ion conductivity} \times \text{lithium ion transport number } (t_{Li}),$$ Equation (f)

wherein the lithium ion transport number ($t_{Li}$) is determined by the following Equation (d):

$$t_{Li} = D_{Li}/(D_{Li} + D_F),$$ Equation (d)

wherein the diffusion coefficients $D_{Li}$ and $D_F$ are each calculated via NMR by the following Equation (c):

$$E = \frac{S}{S_0} = \exp\left(-\gamma^2 g^2 \delta^2 D\left(\Delta - \frac{\delta}{3}\right)\right), \quad \text{Equation (c)}$$

wherein
E is the peak intensity ratio,
S is the peak intensity,
$S_0$ is the peak intensity measured when there is no magnetic field gradient,
γ is the gyromagnetic ratio of nuclear spin,
g is the magnetic field gradient intensity,
δ is the magnetic field gradient irradiation time,
D is the diffusion coefficient $D_{Li}$ or $D_F$, and
Δ is the time interval between magnetic field irradiations.

\* \* \* \* \*